United States Patent
Nakayama et al.

(10) Patent No.: US 8,440,195 B2
(45) Date of Patent: May 14, 2013

(54) INHIBITION OF CD69 FOR TREATMENT OF INFLAMMATORY CONDITIONS

(75) Inventors: Toshinori Nakayama, Chiba (JP); Akihiro Hasegawa, Ube (JP); Mutsunori Shirai, Ube (JP)

(73) Assignees: National University Corporation Chiba University, Chiba (JP); National University Corporation Yamaguchi University, Yamaguchi (JP)

( * ) Notice: Subject to any disclaimer, the term of this patent is extended or adjusted under 35 U.S.C. 154(b) by 0 days.

(21) Appl. No.: 12/945,153

(22) Filed: Nov. 12, 2010

(65) Prior Publication Data
US 2012/0121503 A1 May 17, 2012

(51) Int. Cl.
*A61K 39/395* (2006.01)

(52) U.S. Cl.
USPC ...................................... 424/144.1; 424/183.1

(58) Field of Classification Search .................. None
See application file for complete search history.

(56) References Cited

U.S. PATENT DOCUMENTS

| 7,618,632 | B2 * | 11/2009 | Collins et al. | 424/144.1 |
| 2005/0014224 | A1 * | 1/2005 | Collins et al. | 435/69.1 |
| 2006/0233797 | A1 * | 10/2006 | Gujrathi | 424/144.1 |

FOREIGN PATENT DOCUMENTS

WO  WO 2004069183 A2 *  8/2004

OTHER PUBLICATIONS

Ziegler et al., Stem Cells. Sep. 1994;12(5):456-65.*
Marzio et al., Immunopharm and Immunotox., 21(3), 565-582 (1999).*
Yokoyama et al., J. of Immunology, vol. 141, 369-376, No. 2, Jul. 15, 1988.*
Radulovic et al., The Journal of Immunology, 2012, 188: 2001-2013.*
Hall et al. (Dig Dis Sci (2011) 56:79-89).*
Strom et al. (Therapeutic Immunology edited by Austen et al., Blackwell Science, Cambridge, MA, 1996; pp. 451-456).*
Gunter Muller, Pharmacology 2010; 86:92-116.*
Martin et al., J Allergy Clin Immunol. Aug. 2010;126(2):355-65.*
Murata et al., "CD69-null mice protected from arthritis induced with anti-type II collagen antibodies," International Immunology, vol. 15, No. 8, 2003, pp. 987-992.
Miki-Hosokawa et al., "CD69 Controls the Pathogenesis of Allergic Airway Inflammation," The Journal of Immunology, No. 183, 2009, pp. 8203-8215.

* cited by examiner

*Primary Examiner* — Zachary Skelding
(74) *Attorney, Agent, or Firm* — Kilyk & Bowersox, P.L.L.C.

(57) ABSTRACT

A method of treating or reducing at least one inflammatory condition or the susceptibility to at least one inflammatory condition is provided involving administering at least one CD69 antagonist to a subject, wherein the subject has been diagnosed with at least one inflammatory condition, or a susceptibility to the same. CD69 antagonists can include one or more of an anti-CD69 antibody, an anti-CD69 aptamer, a CD69 mRNA antagonist, and a small molecule pharmaceutical.

17 Claims, 13 Drawing Sheets

A

B

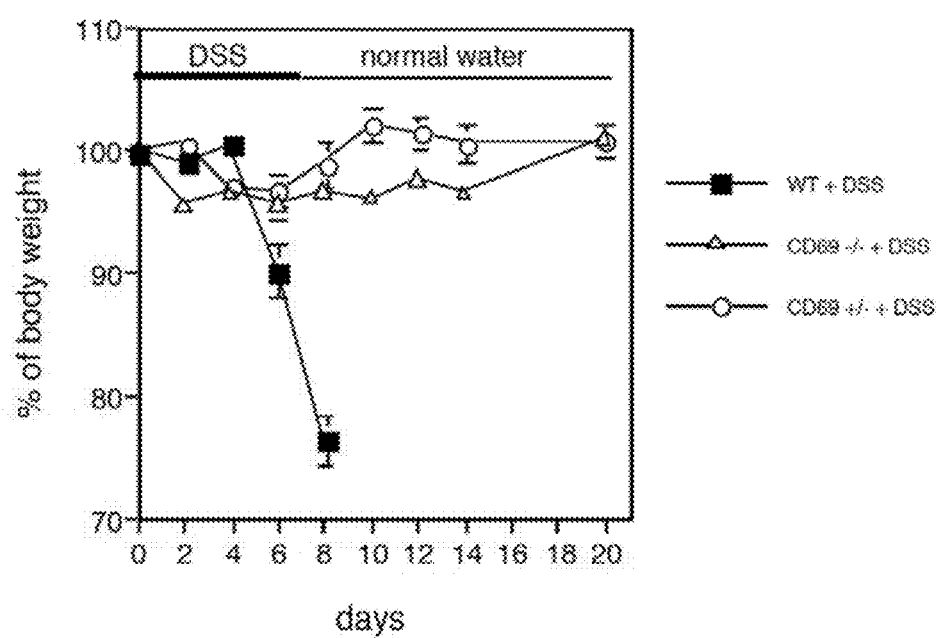

A

B

C
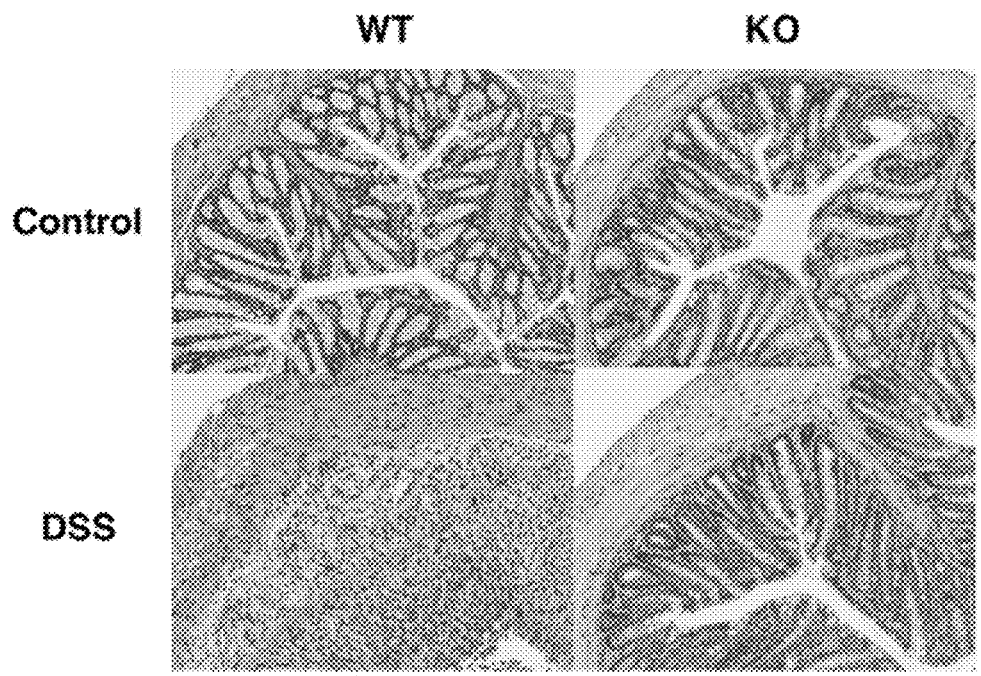
D
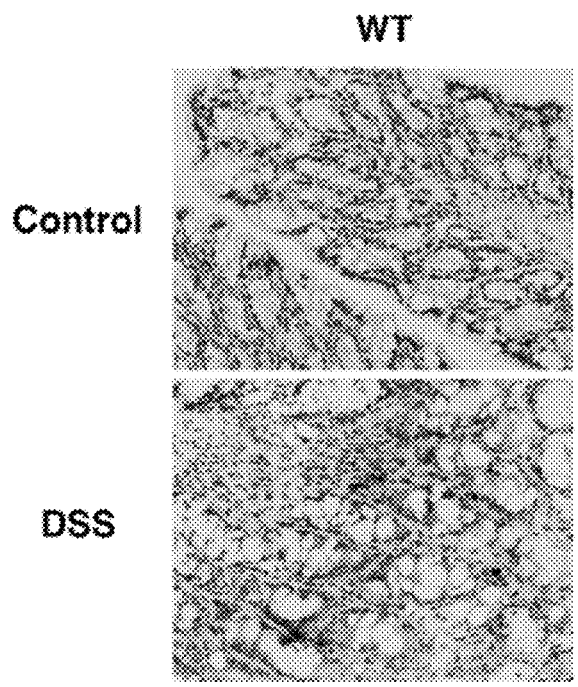

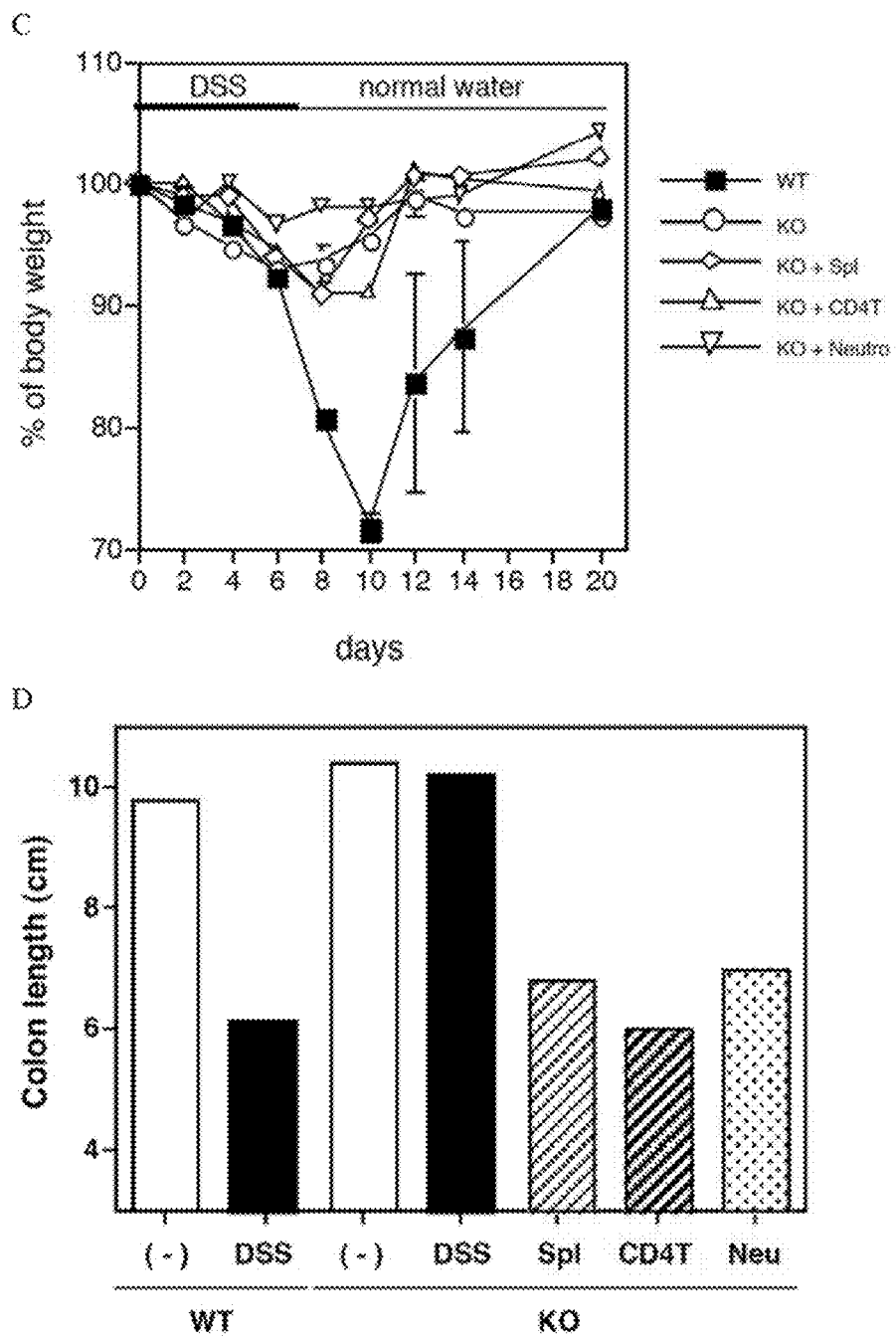

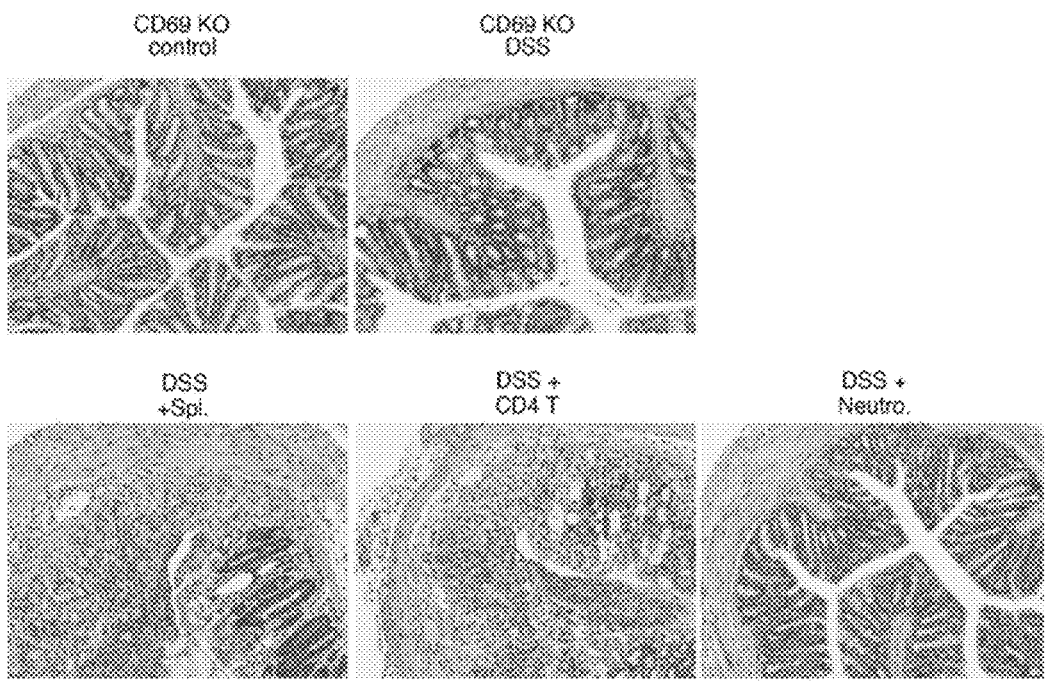

A

B

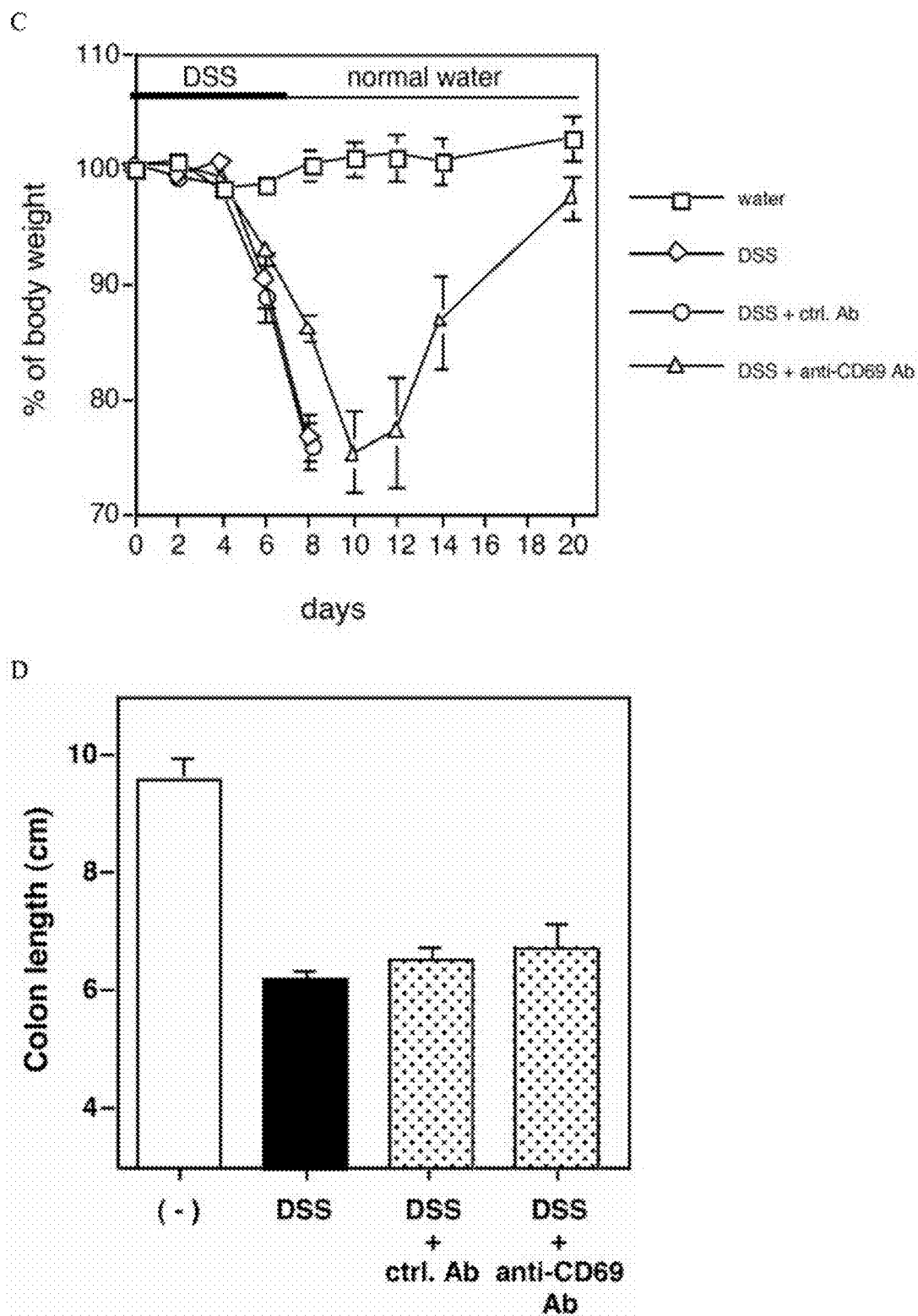

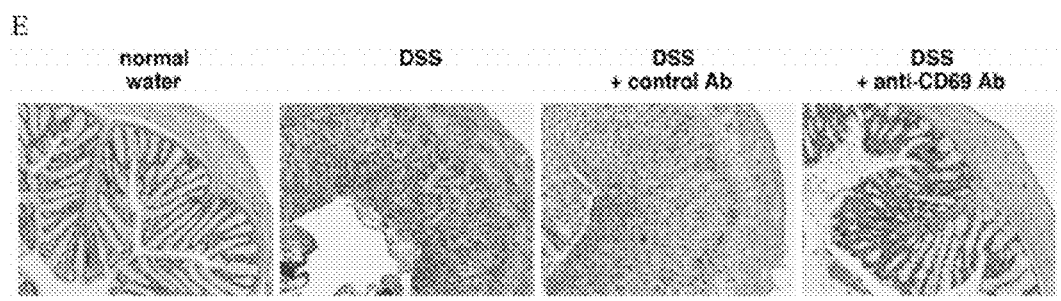

A

B

A

B

INHIBITION OF CD69 FOR TREATMENT OF INFLAMMATORY CONDITIONS

BACKGROUND OF THE INVENTION

The present invention relates to treatment of inflammatory conditions such as colitis and hepatitis.

Human inflammatory bowel disease (IBD), such as Crohn's disease (CD) or ulcerative colitis (UC), are characterized by inflammation in the large and/or small intestine associated with uncontrolled innate and adaptive immunity against normal constituents, including commensal bacteria and various microbial products (Fiocchi et al., *Gastroenterology*, 115:182-205 (1998); McKay, D. M., *Can. J. Gastroenterology*, 13:509-516 (1999); Sartor, *Res Immunol.*, 148: 567-576 (1997); Cong et al., *J. Exp. Med.*, 187:855-864 (1998); Maaser, et al., *Z Gastroenterol.*, 40:525-529 (2002)). Imbalance of pro-inflammatory cytokines in innate immunity has been demonstrated to play a role in the pathogenesis of IBD (Reinecker et al., *Clin. Exp. Immunol.*, 94:174-181 (1993)). Disregulated CD4 T cells in adaptive immunity have also been postulated to play a role in the pathogenesis of IBD (Fuss et al., *J. Immunol.*, 157:1261-1270 (1996); Braegger et al., *Ann. Allergy*, 72:135-141 (1994); Monteleone et al., *Gastroenterology*, 112:1169-78 (1997); Parronchi et al., *Am. J. Pathol.* 150:823-832 (1997)). Responding T cells exhibit a T helper type 1 (Th1) phenotype capable of producing interferon (IFN)-gamma in CD whereas Th2 cytokines are closely associated with UC (Fuss et al., *J. Immunol.*, 157:1261-1270 (1996); Braegger et al., *Ann. Allergy*, 72:135-141 (1994); Monteleone et al., *Gastroenterology*, 112:1169-78 (1997); Parronchi et al., *Am. J. Pathol.* 150:823-832 (1997)).

A widely used animal model for UC is dextran sodium sulfate (DSS)-induced colitis. Mice that are exposed to DSS in their drinking water develop an inflammation of the colon displaying symptoms such as diarrhea, rectal bleeding, and weight loss. The histological phenotype of the acute phase of DSS-induced colitis is characterized by epithelial cell lesions and acute inflammation mainly consisting of infiltrating granulocytes and macrophages (Cooper et al., *Lab Invest*, 69:238-249 (1993); Okayasu et al., *Gastroenterology*, 98:694-702 (1990)). Lymphocytes have been described as not necessary for the acute inflammatory phase of DSS-induced colitis. Mice lacking T cells, however, do not fully recover from colitis (Dieleman et al., *Gastroenterology*, 107:1643-1652 (1994); Tsuchiya et al., *J. Immunol.*, 171:5507-5513 (2003)). Exposure of animals to several cycles of DSS results in the development of chronic colitis that is associated with lymphocyte infiltrates of CD4 T lymphocytes and B cells (Dieleman et al., *Clin. Exp. Immunol.*, 114:385-391 (1998); Teramoto et al., *Clin. Exp. Immunol.*, 139:421-428 (2005)). A role for T lymphocytes in the remission of DSS-induced colitis is not known.

In addition to cytokine expression, chemokines and their receptors also contribute to the regulation of intestinal immune responses and mucosal inflammation. The CC chemokine receptors CCR2 and CCR5 are involved in both monocyte-mediated and macrophage-mediated immune responses, and in the regulation of T cell migration and activation. Mice deficient in CCR2 or CCR5 are protected from DSS-induced colitis (Andres et al., *J. Immunol.*, 164:6303-6312 (2000)). Certain cytokines (such as IL-1β) contribute to disease progression and tissue damage in human inflammatory bowel disease.

T cell-mediated immune responses play a role in the development and progression of various liver diseases, including autoimmune hepatitis, viral infection, and alcoholic hepatitis (Heneghan et al., *Hepatology*, 35:7-13 (2002); Bogdanos et al., *Dig. Liver Dis.*, 32:440-446 (2000); Chang, K. M. et al., *Hepatology*, 33:267-276 (2001); Chedid et al., *Gastroenterology*, 105:254-266 (1993); Kita et al., *Gastroenterology*, 120:1485-1501 (2001); Rehermann et al., *Curr. Top. Microbiol. Immunol.*, 242:299-325 (2000); Eggink et al., *Clin. Exp. Immunol.*, 50:17-24 (1982)). Concanavalin A (ConA)-induced hepatitis is a murine model of autoimmune or viral hepatitis that shares several pathological properties with human autoimmune hepatitis and viral hepatitis (Lohr et al., *Hepatology*, 24:1416-1421 (1996)). ConA-induced hepatitis also has been used as a model of T cell-mediated liver injury (Tiegs et al., *A. J. Clin. Invest.*, 90:196-203 (1992)). These liver diseases are associated with the infiltration of various lymphocyte subsets including activated T cells. The infiltration of CD4 T cells into the liver is involved in human autoimmune and virus hepatitis (Chang et al., *Hepatology*, 33:267-276, 23 (2001); Rehermann et al., *Curr. Top. Microbiol. Immunol.*, 242:299-325 (2000); Eggink et al., *Clin. Exp. Immunol.*, 50:17-24 (1982)). T cells have a documented role in the pathogenesis of ConA-induced hepatitis including the induction and effector phases (Tiegs et al., *J. Clin. Invest.*, 90:196-203 (1992); Kusters et al., *Gastroenterology*, 111: 462-471 (1996); Mizuhara et al., *Hepatology*, 23:1608-1615 (1996); Toyonaga et al., *Proc. Natl. Acad. Sci. U.S.A.*, 91: 614-618 (1994)). Pre-treatment with T cell-specific antibodies or immunosuppressive agents, such as anti-Thy-1, anti-CD4 mAb, FK506, or cyclosporine A, inhibited ConA-induced hepatitis, indicating that CD4 T cells and their activation of TCR-mediated signaling are involved in the induction of ConA-induced hepatitis (Tiegs et al., *J. Clin. Invest.*, 90:196-203 (1992)). In addition, IFN-gamma appears to be involved in the development of ConA-induced hepatitis (Kusters et al., *Gastroenterology*, 111:462-471 (1996); Mizuhara et al., *Hepatology*, 23:1608-1615 (1996); Toyonaga et al., *Proc. Natl. Acad. Sci. U.S.A.*, 91:614-618 (1994)). NKT cells and their production of IFN-gamma play a role in the development of ConA-induced hepatitis (Kaneko et al., *J. Exp. Med.*, 191:105-114 (2000)).

CD69 (also known as early T cell activation antigen p60; see Mendelian Inheritance in Man I.D. No. *107273) is a type II membrane protein expressed as a homodimer of heavily glycosylated subunits (Ziegler et al., *Eur. J. Immunol.*, 23:1643-1648 (1993)). Both T and B cells express CD69 within a few hours after stimulation. CD69 is an early activation marker antigen of lymphocytes (Testi et al., *Immunol. Today*, 15:479-483 (1994)). Freshly prepared thymocytes undergoing selection events express CD69 (Nakayama et al., *J. Immunol.*, 168:87-94 (2002); Feng et al., *Int. Immunol.*, 14:535-544 (2002)). There may be regulatory roles for CD69 expression in T cell development in the thymus, as well as a mild effect on B cell development (Lauzurica et al., *Blood*, 95:2312-2320 (2000)). Constitutive expression of CD69 has been noted in platelets, and activated neutrophils and eosinophils express CD69 on their cell surface. CD69 may have regulatory roles in a collagen-induced arthritis model and an anti-collagen antibody-induced arthritis model, possibly involving multiple target processes (Sancho et al., *J. Clin. Invest.*, 112:872-882 (2003); Murata et al., *Int. Immunol.*, 15:987-992 (2003)). The role of CD69 in other inflammatory models, such as in allergic airway inflammation, however, has not been ascertained. A function of CD69 in lymphocyte trafficking has been proposed (Shiow et al., *Nature*, 440:540-544 (2006)). A role for CD69 in the development of other inflammatory conditions, such as colitis and hepatitis, is unknown.

Accordingly, a need exists for new therapies for treating inflammatory conditions, such as colitis and hepatitis. New anti-inflammatory therapies employing one or more therapeutic compounds against a specific molecular target are sought.

All the patents and publications mentioned above and throughout are incorporated in their entirety by reference herein.

SUMMARY OF THE PRESENT INVENTION

It is therefore a feature of the present invention to provide methods for treating or reducing the susceptibility to inflammatory conditions generally.

Another feature of the present invention is to provide methods for treating or reducing the susceptibility to inflammatory conditions through the inhibition of CD69.

A further feature of the present invention is to provide methods for treating or reducing the susceptibility to colitis and hepatitis specifically.

Another feature of the present invention is the inhibition of CD69 in combination with one or more additional therapies to treat or reduce the susceptibility to an inflammatory condition, such as colitis or hepatitis.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a method of treating or reducing the susceptibility to at least one inflammatory condition involving administering at least one CD69 antagonist to a subject, wherein the subject has been diagnosed with at least one inflammatory condition, or susceptibility to the same, including colitis, hepatitis, a susceptibility to colitis, a susceptibility to hepatitis, or any combination thereof, in an amount effective to treat or reduce the susceptibility to the at least one inflammatory condition.

Any number of CD69 antagonists may be employed, alone, or in combination with other therapies for treating or reducing the susceptibility to at least one inflammatory condition. CD69 antagonists can include one or more of an anti-CD69 antibody, an anti-CD69 aptamer, a CD69 mRNA antagonist, a small molecule pharmaceutical, or any combination thereof. Administration of at least one CD69 antagonist, alone, or in combination with one or more therapies, can be continued when one or more symptoms of an inflammatory condition, such as colitis or hepatitis persists, or can be discontinued when such symptoms decrease or disappear. A combination or two or more CD69 antagonists or one or more CD69 antagonists with one or more therapies can synergistically decrease one or more symptoms of an inflammatory condition.

It is to be understood that both the foregoing general description and the following detailed description are exemplary and explanatory only and are intended to provide a further explanation of the present invention, as claimed.

The accompanying drawings, which are incorporated in and constitute a part of this application, illustrate some of the embodiments of the present invention and together with the description, serve to explain the principles of the present invention.

DETAILED DESCRIPTION OF THE PRESENT INVENTION

Figure 1:
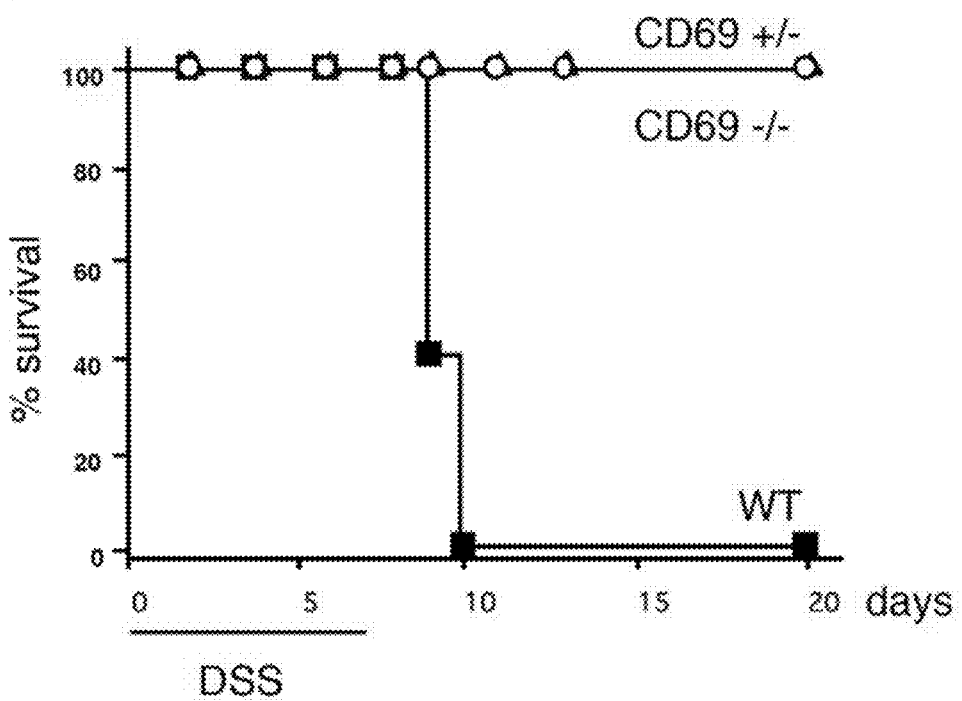
FIG. 1A is a graph that shows data for inhibition of DSS-induced colitis in CD69 knock-out (KO) mice. Colitis is induced by giving animals 4% DSS in drinking water for 7 days followed by normal drinking water. Survival rates of CD69−/−, CD69+/− and wild-type (WT) mice during DSS-induced acute colitis are provided. Survival is recorded daily (n=10 per group).
FIG. 1B is a graph that shows further data for the experiment described for FIG. 1A. Changes in the disease activity index over the course of DSS treatment in CD69−/−, CD69+/− and WT mice are shown.
FIG. 1C is a graph that shows further data for the experiment described for FIG. 1A. Changes in the body weight (%) over the course of DSS treatment in CD69−/−, CD69+/− and WT mice are shown. Data are presented as the mean with SEM (n=10 per group; *p<0.05).
Figure 1:
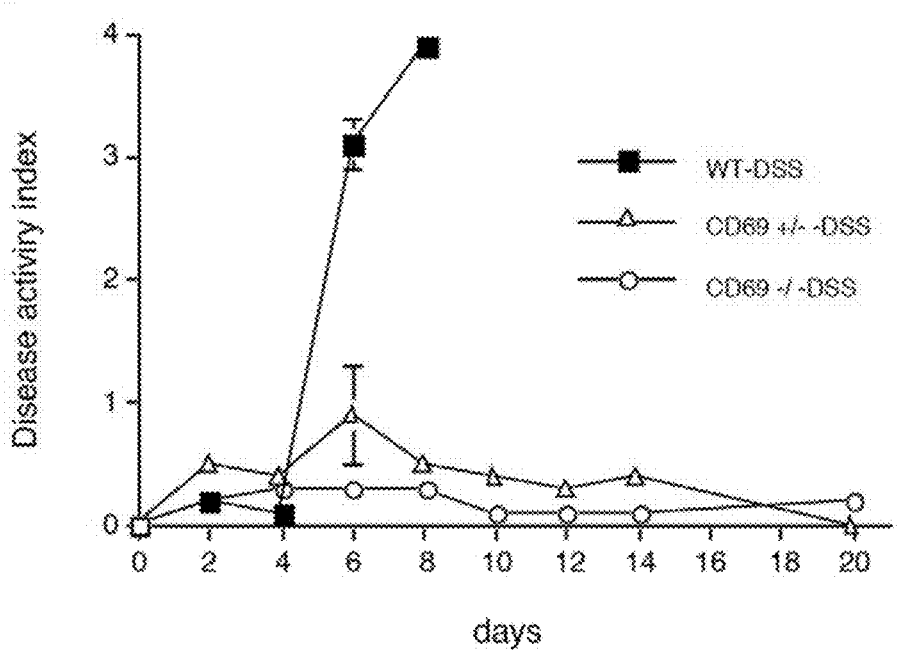

In accordance with the present invention, a method of treating or reducing the susceptibility to at least one inflammatory condition is provided involving administering at least one CD69 antagonist to a subject, wherein the subject has been diagnosed with at least one inflammatory condition, or a susceptibility to the same, including colitis, hepatitis, a susceptibility to colitis, a susceptibility to hepatitis, or any combination thereof, in an amount effective to treat or reduce the inflammation and/or the susceptibility to the at least one inflammatory condition.

When the condition is colitis, the method can further include monitoring at least one symptom of colitis. Examples of colitis symptoms include epithelial cell lesions, acute inflammation, diarrhea, rectal bleeding, and/or weight loss. Colitis symptoms can include abdominal pain, abdominal cramps, an urgent need to have a bowel movement, fever, and/or loss of hunger. The method can further include continuing administration if the at least one symptom persists, falls within a given range, or remains above or below a threshold value; or discontinuing administration if the at least one symptom fails to persist, fails to fall within a given range, or no longer remains above or below a threshold value. Any suitable test can be used for diagnosis of or monitoring of colitis or a susceptibility to the same. Examples of such tests include colonoscopy, biopsy, barium enema X-ray, abdominal X-ray, blood tests for infection or inflammation, stool sample analysis for blood, infection, and/or white blood cell levels and antigens.

Administration of the CD69 antagonist can be combined with one or more anti-colitis therapies. Examples of additional anti-colitis therapies can include medications such as at least one anti-diarrheal medication, at least one aminosalicylate, at least one corticosteroid, at least one immunosuppressant, or any combination thereof. Examples of anti-diarrheal medications include loperamide or salts thereof such as loperamide hydrochloride. Aminosalicylates can include salts thereof such as aminosalicylate sodium. Corticosteroids can include prednisone, prednisolone, methylprednisolone, dexamethasone, salts thereof, or combinations thereof. Immunosuppressants can include, for example, cyclosporins, azathioprines, interleukin-2 inhibiting monoclonal antibodies (basiliximab, daclizumab, and muromonab), salts thereof, or combinations thereof.

Any type or types of colitis can be the subject of treatment or reduction in susceptibility. For example, the colitis can be an ulcerative colitis. As colitis is a form of inflammatory bowel disease (IBD), treatment of IBD or a reduction in susceptibility to IBD by administration of a CD69 antagonist is an aspect of the present invention. Crohn's disease is a form of inflammatory bowel disease. A feature of the present invention is the treatment of and/or reduction of susceptibility to Crohn's disease as described herein in respect to colitis. Whereas colitis is usually associated with the colon and rectum, Crohn's disease can affect the digestive tract more generally.

When the condition is hepatitis, the method can further include monitoring at least one symptom of hepatitis. Examples of hepatitis symptoms include at least one of acute inflammation, raised level of aspartate aminotransferase (AST), and/or raised level of alanine aminotransferase (ALT). The method can further include continuing administration if the at least one symptom persists, falls within a given range, or remains above or below a threshold value; or discontinuing administration if the at least one symptom fails to persist, fails to fall within a given range, or no longer remains above or below a threshold value.

Any type or types of hepatitis can be the subject of treatment or reduction in susceptibility. For example, the hepatitis can be hepatitis A, hepatitis B, hepatitis C, or any combination thereof. Symptoms of hepatitis A can include fatigue, fever, muscle soreness, headache, abdominal pain, nausea, appetite loss, weight loss, jaundice, or any combination thereof. Symptoms of hepatitis B can include jaundice, fatigue, mild fever, headache, appetite loss, nausea, vomiting, abdominal pain, diarrhea, constipation, muscle aches, joint pain, skin rash, or any combination thereof. Symptoms of hepatitis C can include fatigue, joint pain, abdominal pain, itchiness, muscle soreness, jaundice, or any combination thereof.

Diagnosis for, or monitoring of, hepatitis or susceptibility to the same can include one or more blood test to study liver function (heightened bilirubin levels, decreased albumin levels, abnormal prothrombin (clotting) time, anti-hepatitis A, B, or C antibodies or antigens, and the like). Diagnosis for, and monitoring of, hepatitis or susceptibility to the same can include one or more tests for heightened enzyme levels in the blood, such as alanine aminotransferase (ALT), aspartate aminotransferase (AST), alkaline phosphatase (ALP), lactic dehydrogenase (LDH). Liver biopsies can also be employed. Pathogenic nucleic acids such as hepatitis viral RNA can be tested for diagnosis purposes and monitoring.

Administration of the CD69 antagonist can be combined with one or more anti-hepatitis therapies. Examples of additional anti-hepatitis A therapies can include at least one vaccine, at least one immunoglobulin, or any combination thereof. Examples of additional anti-hepatitis B therapies can include at least one vaccine, at least one interferon, at least one nucleoside reverse transcriptase inhibitor, or any combination thereof. Interferons can include interferon alfa-2a, interferon alfa-2b, any pegylation thereof, or any combination thereof. Nucleoside reverse transcriptase inhibitors (NR-TIs) can include adefovir, entecavir, lamivudine, telbivudine, any salt thereof, any prodrug thereof, or any combination thereof. Examples of additional anti-hepatitis C therapies can include at least one vaccine, at least one peginterferon, ribavirin, and/or any combination thereof.

The CD69 antagonist administered can include an antibody or a polypeptide containing an antigen-binding fragment of the antibody. The antibody administered can include a monoclonal or polyclonal antibody. The antibody or the polypeptide administered can include an antigen-binding fragment of the antibody that binds to an extracellular domain of CD69. The antibody or polypeptide can inhibit the activity of CD69. The CD69 antagonist can contain a small molecule (low molecular weight) drug, salts, prodrugs, or combinations thereof. The antagonist can inhibit CD69 activity. Any CD69 amino acid sequence can be employed for producing antibodies or aptamers that bind CD69. Examples of such sequences include those sequences, versions thereof, portions thereof, or combinations thereof with Accession Nos. BAF84558, ABM87473, ABM84101, EAW96123, EAW96122, Q53ZX0, AAO63584, AAH07037, NP_001772, Q07108, CAA83017, CAA80298, or AAB46359.

Antibodies specific for an epitope of CD69, for example an extracellular domain of CD69, and polypeptides containing antigen binding fragments thereof are provided as well as methods, uses, compositions, and kits employing the same. A method of forming an antibody specific to an epitope of CD69 or a polypeptide or a fragment thereof is provided. Such a method can contain providing a nucleic acid encoding a CD69 polypeptide or a polypeptide containing an immunologically specific epitope thereof; expressing a CD69 polypeptide comprising a CD69 amino acid sequence or a polypeptide containing an immunologically specific epitope thereof from the isolated nucleic acid; and generating an antibody specific to the polypeptide obtained or a polypeptide containing an antigen binding fragment thereof. An antibody or polypeptide comprising an antigen binding fragment thereof produced by the aforementioned method is provided. An isolated antibody or isolated polypeptide containing an antigen binding fragment thereof that specifically binds an epitope of CD69 containing a CD69 amino acid sequence is provided. Such an antibody can be generated using any acceptable method(s) known in the art. The antibodies as well as kits, methods, and/or other aspects of the present invention employing antibodies can include one or more of the following: a polyclonal antibody, a monoclonal antibody, a chimeric antibody, a single-chain antibody, a monovalent antibody, a diabody, and/or a humanized antibody.

Naturally occurring antibody structural units typically contain a tetramer. Each such tetramer can be composed of two identical pairs of polypeptide chains, each pair having one full-length light" (for example, about 25 kDa) and one full-length "heavy" chain (for example, about 50-70 kDa). The amino-terminal portion of each chain typically includes a variable region of about 100 to 110 or more amino acids that typically is responsible for antigen recognition. The carboxy-terminal portion of each chain typically defines a constant region that may be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. In light and heavy chains, the variable and constant regions can be joined by a "J" region of about 12 or more amino acids, with the heavy chain also including a "D" region of about 10 or more amino acids. See, e.g., *Fundamental Immunology* Ch. 7 (Paul, W., ed., 2nd ed. Raven Press, N.Y. (1989)) (incorporated by reference in its entirety for all purposes). The variable regions of each light/heavy chain pair typically form the antigen binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which may enable binding to a specific epitope. From N-terminal to C-terminal, both light and heavy chain variable regions typically contain the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk *J. Mol. Biol.* 196:901-917 (1987); Chothia et al., *Nature* 342:878-883 (1989).

"Antibody fragments" include a portion of an intact antibody, such as the antigen binding or variable region of the intact antibody. Examples of antibody fragments include Fab, Fab1, F(ab')2, and Fv fragments; diabodies; linear antibodies (Zapata et al., *Protein Eng.* 8(10): 1057-1062 [1995]); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen-combining sites and is still capable of cross-linking antigen. "Fv" is an antibody fragment which contains a complete antigen-recognition and -binding site. This region consists of a dimer of one heavy- and one light-chain variable domain in tight, non-covalent association. A single variable domain (or half of an Fv containing only three CDRs specific for an antigen) can recognize and bind an antigen. "Single-chain Fv" or "sFv" antibody fragments include the VH and VL domains of the antibody, wherein these domains are present in a single polypeptide chain. The Fv polypeptide can further contain a polypeptide linker between the VH and VL domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

Antibodies can be used as probes, therapeutic treatments and other uses. Antibodies can be made by injecting mice, rabbits, goats, or other animals with the translated product or synthetic peptide fragments thereof. These antibodies are useful in diagnostic assays or as an active ingredient in a pharmaceutical composition.

The antibody or polypeptide administered can be conjugated to a functional agent to form an immunoconguate. The functional agent can be a cytotoxic agent such as a chemotherapeutic agent, a toxin (e.g., an enzymatically active toxin of bacterial, fungal, plant, or animal origin, or fragments thereof), or a radioactive isotope (i.e., a radioconjugate), an antibiotic, a nucleolytic enzyme, or any combination thereof. Chemotherapeutic agents can be used in the generation of immunoconjugates, e.g., methotrexate, adriamicin, vinca alkaloids (vincristine, vinblastine, etoposide), doxorubicin, melphalan, mitomycin C, chlorambucil, daunorubicin or other intercalating agents, enzymes, and/or fragments thereof, such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Enzymatically active toxins and fragments thereof that can be used include, for example, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricotheeenes. Any appropriate radionucleotide or radioactive agent known in the art or are otherwise available can be used to produce radioconjugated antibodies.

Conjugates of the antibody and cytotoxic agent can be made using a variety of bifunctional protein-coupling agents such as N-succinimidyl-3-(2-pyridyldithiol)propionate (SPDP); iminothiolane (IT); bifunctional derivatives of imidoesters (such as dimethyl adipimidate HCL); active esters (such as disuccinimidyl suberate); aldehydes (such as glutareldehyde); bis-azido compounds (such as bis(p-azidobenzoyl) hexanediamine); bis-diazonium derivatives (such as bis-(p-diazoniumbenzoyl)-ethylenediamine); diisocyanates (such as tolyene 2,6-diisocyanate); bis-active fluorine compounds (such as 1,5-difluoro-2,4-dinitrobenzene); maleimidocaproyl (MC); valine-citrulline, dipeptide site in protease cleavable linker (VC); 2-amino-5-ureido pentanoic acid PAB=p-aminobenzylcarbamoyl ("self immolative" portion of linker) (Citrulene); N-methyl-valine citrulline where the linker peptide bond has been modified to prevent its cleavage by cathepsin B (Me); maleimidocaproyl-polyethylene glycol, attached to antibody cysteines; N-Succinimidyl 4-(2-pyridylthio)pentanoate (SPP); and N-succinimidyl 4-(N-maleimidomethyl)cyclohexane-1 carboxylate (SMCC). For example, a ricin immunotoxin can be prepared as described in Vitetta et al., Science, 238: 1098 (1987). Carbon-14-labeled 1-isothiocyanatobenzyl-3-methyldiethylene triaminepentaacctic acid (MX-DTPA) is an exemplary chelating agent for conjugation of radionucleotide to the antibody, see WO 94/11026. The antibody can be conjugated to a "receptor" (such as streptavidin) for utilization in tumor pre-targeting wherein the antibody-receptor conjugate is administered to the subject, followed by removal of unbound conjugate from the circulation using a clearing agent and then administration of a "ligand" (e.g., avidin) that is conjugated to a cytotoxic agent (e.g., a radionucleotide).

The antibodies of the present invention can be coupled directly or indirectly to a detectable marker by techniques well known in the art. A detectable marker is an agent detectable, for example, by spectroscopic, photochemical, biochemical, immunochemical, or chemical means. Useful detectable markers include, but are not limited to, fluorescent dyes, chemiluminescent compounds, radioisotopes, electron-dense reagents, enzymes, colored particles, biotin, or dioxigenin. A detectable marker often generates a measurable signal, such as radioactivity, fluorescent light, color, or enzyme activity. Antibodies conjugated to detectable agents may be used for diagnostic or therapeutic purposes. Examples of detectable agents include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody or indirectly, through an intermediate such as, for example, a linker known in the art, using techniques known in the art. See, e.g., U.S. Pat. No. 4,741,900, describing the conjugation of metal ions to antibodies for diagnostic use. Examples of suitable enzymes include horseradish peroxidase, alkaline phosphatase, beta-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferin, and aequorin.

Antibodies useful in practicing the present invention can be prepared in laboratory animals or by recombinant DNA techniques using the following methods. Polyclonal antibodies can be raised in animals by multiple subcutaneous (sc) or intraperitoneal (ip) injections of the gene product molecule or fragment thereof in combination with an adjuvant such as Freund's adjuvant (complete or incomplete). To enhance immunogenicity, it may be useful to first conjugate the gene product molecule or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl, etc.

Alternatively, immunogenic conjugates can be produced recombinantly as fusion proteins.

Animals can be immunized against the immunogenic conjugates or derivatives (such as a fragment containing the target amino acid sequence) by combining about 1 mg or about 1 microgram of conjugate (for rabbits or mice, respectively) with about 3 volumes of Freund's complete adjuvant and injecting the solution intradermally at multiple sites. Approximately 7 to 14 days later, animals are bled and the serum is assayed for antibody titer. Animals are boosted with antigen repeatedly until the titer plateaus. The animal can be boosted with the same molecule or fragment thereof as was used for the initial immunization, but conjugated to a different protein and/or through a different cross-linking agent. In addition, aggregating agents such as alum can be used in the injections to enhance the immune response.

The antibody administered can include a chimeric antibody. The antibody administered can include a humanized antibody. The antibody administered can include a completely humanized antibody. The antibodies can be humanized or partially humanized. Non-human antibodies can be humanized using any applicable method known in the art. A humanized antibody can be produced using a transgenic animal whose immune system has been partly or fully humanized. Any antibody or fragment thereof of the present invention can be partially or fully humanized. Chimeric antibodies can be produced using any known technique in the art. See, e.g., U.S. Pat. Nos. 5,169,939; 5,750,078; 6,020,153; 6,420,113; 6,423,511; 6,632,927; and 6,800,738.

The antibody administered can include a monoclonal antibody, that is, the anti-CD69 antibodies of the present invention that can be monoclonal antibodies. Monoclonal antibodies can be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro. Monoclonal antibodies can be screened as are described, for example, in Harlow & Lane, *Antibodies, A Laboratory Manual*, Cold Spring Harbor Press, New York (1988); Goding, *Monoclonal Antibodies, Principles and Practice* (2d ed.) Academic Press, New York (1986). Monoclonal antibodies can be tested for specific immunoreactivity with a translated product and lack of immunoreactivity to the corresponding prototypical gene product.

Monoclonal antibodies can be prepared by recovering spleen cells from immunized animals and immortalizing the cells in conventional fashion, e.g., by fusion with myeloma cells. The clones are then screened for those expressing the desired antibody. The monoclonal antibody preferably does not cross-react with other gene products. After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal. The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the present invention can be readily isolated and sequenced using conventional procedures (e.g., by using oligonucleotide probes that are capable of binding specifically to genes encoding the heavy and light chains of murine antibodies). The hybridoma cells of the present invention can serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences or by covalently joining to the immunoglobulin coding sequence all or part of the coding sequence for a non-immunoglobulin polypeptide. Such a non-immunoglobulin polypeptide can be substituted for the constant domains of an antibody of the present invention, or can be substituted for the variable domains of one antigen-combining site of an antibody of the invention to create a chimeric bivalent antibody. Preparation of Antibodies Using Recombinant DNA Methods Such as the Phagemid Display Method, can be accomplished using commercially available kits, as for example, the Recombinant Phagemid Antibody System available from Pharmacia (Uppsala, Sweden), or the SurfZAP™ phage display system (Stratagene Inc., La Jolla, Calif.).

Also included in the present invention are hybridoma cell lines, transformed B cell lines, and host cells that produce the monoclonal antibodies of the present invention; the progeny or derivatives of these hybridomas, transformed B cell lines, and host cells; and equivalent or similar hybridomas, transformed B cell lines, and host cells. Examples of hybridoma cells lines include without limitation H1.2F3 (BioLegend, Inc., San Diego, Calif.).

The antibodies can be diabodies. The term "diabodies" refers to small antibody fragments with two antigen-binding sites, which fragments include a heavy-chain variable domain (VH) connected to a light-chain variable domain (VL) in the same polypeptide chain (Vn-VL). By using a linker that is too short to allow pairing between the two domains on the same chain, the domains can be forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The antibody administered can include a single-chain antibody. The antibodies can be monovalent antibodies. Methods for preparing monovalent antibodies are well known in the art. For example, one method involves recombinant expression of immunoglobulin light chain and modified heavy chain. The heavy chain can be truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies. Digestion of antibodies to produce fragments thereof, particularly, Fab fragments, can be accomplished using routine techniques known in the art.

The antibodies can be bispecific. Bispecific antibodies that specifically bind to one protein and that specifically bind to other antigens relevant to pathology and/or treatment are produced, isolated, and tested using standard procedures that have been described in the literature. [See, e.g., Pluckthun & Pack, *Immunotechnology*, 3:83-105 (1997); Carter, et al., *J. Hematotherapy*, 4:463-470 (1995); Renner & Pfreundschuh, *Immunological Reviews*, 1995, No. 145, pp. 179-209; Pfreundschuh U.S. Pat. No. 5,643,759; Segal, et al., *J. Hematotherapy*, 4:377-382 (1995); Segal, et al., *Immunobiology*, 185: 390-402 (1992); and Bolhuis, et al., *Cancer Immunol. Immunother.*, 34:1-8 (1991)].

The antibodies disclosed herein can be formulated as immunoliposomes. Liposomes containing the antibody are prepared by methods known in the art. such as described in Epstein et al., *Proc. Natl. Acad. Sci. USA*, 82: 3688 (1985); Hwang et al., *Proc. Natl. Acad. Sci. USA* 77: 4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse-phase evaporation method with a lipid composition containing phosphatidylcholine, cholesterol, and PEG-derivatized phosphatidylethanolamine (PEG-PE). Liposomes can be extruded through filters of defined pore size to yield liposomes with the desired diameter. Fab' fragments of the antibody of the present invention can be conjugated to the liposomes as described in Martin et al., *J. Biol. Chem.*, 257: 286-288 (1982) via a disulfide-interchange reaction. A chemotherapeutic agent (such as Doxorubicin) is optionally contained within the liposome. See Gabizon et al, *J. National Cancer Inst.*, 81(19): 1484 (1989).

The CD69 antagonist can include an aptamer that binds CD69. The aptamer can contain one or more of a nucleic acid, a RNA, a DNA, and an amino acid. Aptamers can be selected and produced using any suitable technique or protocol. For example, oligonucleotide libraries with variable regions ranging from 18 to 50 nucleotides in length can be used as templates for run-off transcription reactions to generate random pools of RNA aptamers. This aptamer pool can then be exposed to unconjugated matrix to remove non-specific interacting species. The remaining pool is then incubated with an immobilized target. The majority of aptamer species in this pool can have low affinity, for the target can be washed away leaving a smaller, more specific pool bound to the matrix. This pool can then be eluted, precipitated, reverse transcribed, and used as a template for run-off transcription. After five rounds of selection, aliquots can be removed that are cloned and sequenced. Selection can be continued until similar sequences are reproducibly recovered.

Aptamer production can be performed using a bead-based selection system. In this process, a library of beads is generated in which each bead is coated with a population of aptamers with identical sequences composed of natural and modified nucleotides. This bead library, which can contain greater than 100,000,000 unique sequences, can be incubated with a peptide that corresponds to CD69, or a portion thereof, e.g., an extracellular domain, that is conjugated with a tag such as a fluorescent dye. After washing, beads that demonstrate the highest binding affinity can be isolated and aptamer sequences can be determined for subsequent synthesis.

The CD69 antagonist administered can include a mRNA antagonist. Examples of mRNA antagonists can include at least one siRNA or at least one ribozyme. In accordance with the present invention, the CD69 antagonist can be a therapeutic nucleic acid, such as a siRNA, can target a CD69 nucleotide sequence, complements thereof, or any combination thereof. Any suitable CD69 sequence can be employed. CD69 target sequences of the synthetic siRNAs can be designed against a human CD69 nucleotide sequence, or any portion or combination thereof, with Accession No. NM_001781, NR_026672, NR_026671, AK303383, AK303174, AK291869, DQ896474, DQ893175, CH471094, AY238518, BC007037, AC007068, Z38109, Z30426, Z22576, or L07555, or recognize all or a subset of CD69 transcript variants.

The CD69 antagonist employed in the present invention can cause a decrease in the expression of CD69. A CD69 mRNA antagonist is an example of such an antagonist. The CD69 antagonist can be a nucleic acid at least 10 nucleotides in length that specifically binds to and is complementary to a target nucleic acid encoding CD69 or a complement thereof, wherein the administration of the CD69 antagonist involves introducing the nucleic acid into a cell of the subject. RNA interference (RNAi) can be employed and the CD69 antagonist can be a small interfering RNA (siRNA). The administration of the CD69 antagonist involves introducing into a cell of a subject, wherein the cell is capable of expressing CD69 as an effective amount of a small interfering RNA (siRNA) nucleic acid for a time and under conditions sufficient to interfere with expression of CD69. siRNA nucleic acids can include overhangs. That is, not all nucleotides need bind to the target sequence. The siRNA nucleic acids can contain RNA. The siRNA nucleic acid can also contain DNA, that is, deoxyribonucleic acid nucleotides. Any type of suitable small interfering RNA can be employed. Endogenous microRNA (miRNA) can be employed. Other RNA interference agents that can be used in accordance with the present invention include short hairpin RNA (shRNA), trans-acting siRNAs (tasiRNAs), repeat-associated siRNAs (rasiRNAs), small-scan (scn)RNAs, and Piwi-interacting (pi)RNAs. RNA interference nucleic acids employed can be at least 10, at least 15, 16, 17, 18, 19, 20, 21, 22, 23, 24, 25, 26, 27, 28, 29, 30, 31, 32, 33, 34, at least 35, and/or between 40-50 nucleotides in length. RNAi agent can also include one or more deoxyribonucleotide. The RNAi agent, for example, siRNA or shRNA, can be included as a cassette by a larger nucleic acid construct such as an appropriate vector system. Examples of such vectors systems include lentiviral and adenoviral vector systems. An example of a suitable system is described in Aagaard et al., *Mol. Ther.*, 15(5):938-45 (2007). When present as part of a larger nucleic acid construct, the resulting nucleic acid can be longer than the included RNAi nucleic acid, for example, greater than 50 nucleotides in length. The RNAi agent employed may or may not cleave the target mRNA.

In addition or in the alternative to RNA interference, other nucleic acid antagonists can be employed. The CD69 antagonist can be a ribozyme that specifically cleaves an RNA molecule transcribed from a gene encoding CD69, wherein the ribozyme contains a target substrate binding site, a catalytic sequence within the substrate binding site, wherein the substrate binding site is complementary to a portion of an RNA molecule transcribed from the CD69 gene. The CD69 antagonist can be an antisense nucleic acid containing a nucleotide sequence complementary to at least 8 nucleotides of a nucleic acid encoding CD69 or a complement thereof. The antisense nucleic acid can be complementary to a CD69 sequence that is of sufficient length and sequence content such that the antisense nucleic acid does not crossreact with non-CD69 nucleotide sequences. Cross-reaction can occur but not cause a substantial deleterious side effect.

The CD69 antagonist administered can include a small molecule pharmaceutical. For example, CD69-disabling small peptide mimetics can be employed. Such mimetics can be constructed to resemble secondary structural features of the targeted protein 69.

In accordance with the present invention, two or more CD69 antagonists can be administered. At least one CD69 antagonist can be administered in combination with one or more additional therapies directed to colitis, hepatitis, a susceptibility to colitis, a susceptibility to hepatitis, or any combination thereof. The administration of two or more therapies, including one or more CD69 antagonists, can be simultaneous, sequential, or in combination. Accordingly, when two or more therapies are administered, they need not be administered simultaneously or in the same way or in the same dose. When administered simultaneously, the two or more therapies can be administered in the same composition or in different compositions. The two or more therapies can be administered using the same route of administration or different routes of administration. When administered at different times, the therapies can be administered before or after each other. Administration order of the two or more therapies can be alternated. The respective doses of the one or more therapies can be varied over time. The type of one or more therapy can be varied over time. When administered at separate times, the separation of the two or more administrations can be any time period. If administered multiple times, the length of the time period can vary. The separation between administration of the two or more two or more therapies can be 0 seconds, 1 second, 5 seconds, 10 seconds, 30 seconds, 1 minute, 5 minutes, 10 minutes, 15 minutes, 20 minutes, 30, minutes, 45 minutes, 1 hour, 1.5 hours, 2 hours, 2.5 hours, 3 hours, 4 hours, 5 hours, 7.5 hours, 10 hours, 12 hours, 15 hours, 18 hours, 21 hours, 24 hours, 1.5 days, 2 days, 3 days, 4 days, 5 days, 6 days, 7 days, 10 days, 2 weeks, 3 weeks, 4 weeks, one month, 6 weeks, 8 weeks, three months, six months, 1 year or longer.

Two or more CD69 antagonists can act synergistically to treat or reduce the susceptibility to the at least one inflammatory condition. At least one CD69 antagonist and the one or more additional therapies can act synergistically to treat or reduce the susceptibility to the at least one inflammatory condition. Two or more therapies, including one or more CD69 antagonist, can be administered in synergistic amounts. Accordingly, the administration of two or more therapies can have a synergistic effect on the decrease in one or more symptoms of colitis and/or hepatitis, or other inflammatory condition, whether administered simultaneously, sequentially, or in any combination. A first therapy can increase the efficacy of a second therapy greater than if second therapy was employed alone, or a second therapy increases the efficacy of a first therapy, or both. The effect of administering two or more therapies can be such that the effect on decreasing one or more symptom of colitis and/or hepatitis is greater than the additive effect of each being administered alone. When given in synergistic amounts, one therapy can enhance the efficacy of one or more other therapy on the decrease in one or more symptoms of colitis and/or hepatitis, even if the amount of one or more therapy alone would have no substantial effect on one or more symptom of colitis and/or hepatitis. Measurements and calculations of synergism can be performed as described in Teicher, "Assays for In Vitro and In Vivo Synergy," in *Methods in Molecular Medicine*, vol. 85: Novel Anticancer Drug Protocols, pp. 297-321 (2003) and/or by calculating the combination index (CI) using CalcuSyn software.

Exact formulation, route of administration and dosage can be chosen by the individual physician in view of the patient's condition. [See, e.g., Fingl et. al., in *The Pharmacological Basis of Therapeutics,* 1975, Ch. 1 p. I.] The attending physician can determine when to terminate, interrupt, or adjust administration due to toxicity, or to organ dysfunctions. Conversely, the attending physician can also adjust treatment to higher levels if the clinical response were not adequate, precluding toxicity. The magnitude of an administrated dose in the management of disorder of interest will vary with the severity of the disorder to be treated and the route of administration. The severity of the disorder can, for example, be evaluated, in part, by standard prognostic evaluation methods. The dose and dose frequency, can vary according to the age, body weight, and response of the individual patient. A program comparable to that discussed above can be used in veterinary medicine.

Use of pharmaceutically acceptable carriers to formulate the compounds herein disclosed for the practice of the invention into dosages suitable for systemic administration is within the scope of the present invention. With proper choice of carrier and suitable manufacturing practice, the compositions relevant to the present invention, in particular, those formulated as solutions, can be administered parenterally, such as by intravenous injection. The compounds can be formulated readily using pharmaceutically acceptable carriers well known in the art into dosages suitable for oral administration. Such carriers enable the compounds relevant to the present invention to be formulated as tablets, pills, capsules, liquids, gels, syrups, slurries, tablets, dragees, solutions, suspensions and the like, for oral ingestion by a patient to be treated.

The therapeutic agent can be prepared in a depot form to allow for release into the body to which it is administered is controlled with respect to time and location within the body (see, for example, U.S. Pat. No. 4,450,150). Depot forms of therapeutic agents can be, for example, an implantable composition containing the therapeutic agent and a porous or non-porous material, such as a polymer, wherein the therapeutic agent is encapsulated by or diffused throughout the material and/or degradation of the non-porous material. The depot is then implanted into the desired location within the body and the therapeutic agent is released from the implant at a predetermined rate.

The therapeutic agent that is used in the present invention can be formed as a composition, such as a pharmaceutical composition containing a carrier and a therapeutic compound. Pharmaceutical compositions containing the therapeutic agent can include more than one therapeutic agent. The pharmaceutical composition can alternatively contain a therapeutic agent in combination with other pharmaceutically active agents or drugs.

The carrier can be any suitable carrier. For example, the carrier can be a pharmaceutically acceptable carrier. With respect to pharmaceutical compositions, the carrier can be any of those conventionally used with consideration of chemico-physical considerations, such as solubility and lack of reactivity with the active compound(s), and by the route of administration. In addition to, or in the alternative to, the following described pharmaceutical compositions, the therapeutic compounds of the present inventive methods can be formulated as inclusion complexes, such as cyclodextrin inclusion complexes, or liposomes.

The pharmaceutically acceptable carriers described herein, for example, vehicles, adjuvants, excipients, and diluents; are well-known to those skilled in the art and are readily available to the public. The pharmaceutically acceptable carrier can be chemically inert to the active agent(s) and one which has no detrimental side effects or toxicity under the conditions of use. The choice of carrier can be determined in part by the particular therapeutic agent, as well as by the particular method used to administer the therapeutic compound. There are a variety of suitable formulations of the pharmaceutical composition of the present invention. The following formulations for oral, aerosol, parenteral, subcutaneous, transdermal, transmucosal, intestinal, intramedullary injections, direct intraventricular, intravenous, intranasal, intraocular, intramuscular, intraarterial, intrathecal, intraperitoneal, rectal, and vaginal administration are exemplary and are in no way limiting. More than one route can be used to administer the therapeutic agent, and in some instances, a particular route can provide a more immediate and more effective response than another route. Depending on the specific disorder being treated, such agents can be formulated and administered systemically or locally. Techniques for formulation and administration may be found in *Remington's Pharmaceutical Sciences,* 18th ed., Mack Publishing Co., Easton, Pa. (1990).

Formulations suitable for oral administration can include (a) liquid solutions, such as an effective amount of the inhibitor dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant. Capsule forms can be of the ordinary hard or soft shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can contain the inhibitor in a flavor, usually sucrose and acacia or tragacanth, as well as pastilles containing the inhibitor in an inert base, such as gelatin and glycerin, or sucrose and acacia, emulsions, gels, and the like containing, in addition to, such excipients as are known in the art.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers can be added.

The therapeutic agent, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressurized preparations, such as in a nebulizer or an atomizer. Such spray formulations also may be used to spray mucosa. Topical formulations are well known to those of skill in the art. Such formulations are particularly suitable in the context of the invention for application to the skin.

Injectable formulations are in accordance with the present invention. The parameters for effective pharmaceutical carriers for injectable compositions are well-known to those of ordinary skill in the art [see, e.g., *Pharmaceutics and Pharmacy Practice, J. B. Lippincott Company, Philadelphia, Pa., Banker and Chalmers, eds., pages* 238250 (1982), and *ASHP Handbook on Injectable Drugs,* Toissel, 4th ed., pages 622 630 (1986)]. For injection, the agents of the present invention can be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Formulations suitable for parenteral administration can include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The therapeutic agent can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, poly(ethyleneglycol) 400, glycerol, dimethylsulfoxide, ketals such as 2,2-dimethyl-1,3-dioxolane-4-methanol, ethers, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations can contain from about 0.5% to about 25% by weight of the drug in solution. Preservatives and buffers can be used. In order to minimize or eliminate irritation at the site of injection, such compositions may contain one or more nonionic surfactants having a hydrophilic-lipophilic balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The therapeutic agent can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

Agents intended to be administered intracellularly may be administered using techniques well known to those of ordinary skill in the art. For example, such agents can be encapsulated into liposomes. Liposomes are spherical lipid bilayers with aqueous interiors. Molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly. Materials and methods described for one aspect of the present invention can also be employed in other aspects of the present invention. For example, a material such a nucleic acid or antibody described for use in screening assays can also be employed as therapeutic agents and vice versa.

The present invention includes the following aspects/embodiments/features in any order and/or in any combination:

1. The present invention relates to a method of treating or reducing at least one inflammatory condition and/or the susceptibility to at least one inflammatory condition comprising:
   administering at least one CD69 antagonist to a subject, wherein the subject has been diagnosed with at least one inflammatory condition, or susceptibility to the same, comprising colitis, hepatitis, a susceptibility to colitis, a susceptibility to hepatitis, or any combination thereof, in an amount effective to treat or reduce the inflammatory condition and/or the susceptibility to the at least one inflammatory condition.
2. The method of any preceding or following embodiment/feature/aspect, wherein the condition comprises colitis.
3. The method of any preceding or following embodiment/feature/aspect, further comprising:
   monitoring at least one symptom of colitis.
4. The method of any preceding or following embodiment/feature/aspect, wherein the at least one symptom comprises at least one of epithelial cell lesions, acute inflammation, diarrhea, rectal bleeding, and/or weight loss.
5. The method of any preceding or following embodiment/feature/aspect, further comprising:
   continuing administration if the at least one symptom persists, falls within a given range, or remains above or below a threshold value; or
   discontinuing administration if the at least one symptom fails to persist, fails to fall within a given range, or no longer remains above or below a threshold value.
6. The method of any preceding or following embodiment/feature/aspect, wherein the symptom comprises at least one of epithelial cell lesions, acute inflammation, diarrhea, rectal bleeding, and weight loss.
7. The method of any preceding or following embodiment/feature/aspect, wherein the condition comprises hepatitis.
8. The method of any preceding or following embodiment/feature/aspect, further comprising:
   monitoring at least one symptom of hepatitis.
9. The method of any preceding or following embodiment/feature/aspect, wherein the symptom comprises at least one of acute inflammation, raised level of aspartate aminotransferase (AST), and raised level of alanine aminotransferase (ALT).
10. The method of any preceding or following embodiment/feature/aspect, further comprising:
    continuing administration if the at least one symptom persists, falls within a given range, or remains above or below a threshold value; or
    discontinuing administration if the at least one symptom fails to persist, fails to fall within a given range, or no longer remains above or below a threshold value.
11. The method of any preceding or following embodiment/feature/aspect, wherein the symptom comprises at least one of acute inflammation, raised level of aspartate aminotransferase (AST), and/or raised level of alanine aminotransferase (ALT).
12. The method of any preceding or following embodiment/feature/aspect, wherein the CD69 antagonist administered comprises an antibody or a polypeptide comprising an antigen-binding fragment of the antibody.
13. The method of any preceding or following embodiment/feature/aspect, wherein the antibody is a chimeric antibody.
14. The method of any preceding or following embodiment/feature/aspect, wherein the antibody is a humanized antibody.
15. The method of any preceding or following embodiment/feature/aspect, wherein the antibody is a completely humanized antibody.
16. The method of any preceding or following embodiment/feature/aspect, wherein the antibody is a monoclonal antibody.
17. The method of any preceding or following embodiment/feature/aspect, wherein the antibody is a polyclonal antibody.
18. The method of any preceding or following embodiment/feature/aspect, wherein the antibody is a single-chain antibody.
19. The method of any preceding or following embodiment/feature/aspect, wherein the antibody or polypeptide is conjugated to a functional agent to form an immunoconguate.
20. The method of any preceding or following embodiment/feature/aspect, wherein the functional agent is a cytotoxic agent that is an antibiotic, a radioactive isotope, a nucleolytic enzyme, a toxin, or any combination thereof.
21. The method of any preceding or following embodiment/feature/aspect, wherein the antibody or the polypeptide, comprising an antigen-binding fragment of the antibody, binds to an extracellular domain of CD69.
22. The method of any preceding or following embodiment/feature/aspect, wherein the CD69 antagonist comprises an aptamer that binds CD69.
23. The method of any preceding or following embodiment/feature/aspect, wherein the aptamer comprises a nucleic acid.
24. The method of any preceding or following embodiment/feature/aspect, wherein the aptamer comprises RNA.
25. The method of any preceding or following embodiment/feature/aspect, wherein the aptamer comprises DNA.
26. The method of any preceding or following embodiment/feature/aspect, wherein the aptamer comprises an amino acid.
27. The method of any preceding or following embodiment/feature/aspect, wherein the CD69 antagonist comprises a mRNA antagonist.
28. The method of any preceding or following embodiment/feature/aspect, wherein the mRNA antagonist comprises RNA interference.
29. The method of any preceding or following embodiment/feature/aspect, wherein the mRNA antagonist comprises a ribozyme.

30. The method of any preceding or following embodiment/feature/aspect, wherein two or more CD69 antagonists are administered.

31. The method of any preceding or following embodiment/feature/aspect, wherein the two or more CD69 antagonists act synergistically to treat or reduce the inflammatory condition and/or the susceptibility to the at least one inflammatory condition.

32. The method of any preceding or following embodiment/feature/aspect, wherein at least one CD69 antagonist is administered in combination with one or more additional therapies directed to colitis, hepatitis, a susceptibility to colitis, a susceptibility to hepatitis, or any combination thereof.

33. The method of any preceding or following embodiment/feature/aspect, wherein the combination of the at least one CD69 antagonist and the one or more additional therapies act synergistically to treat or reduce the susceptibility to the at least one inflammatory condition.

34. The method of any preceding or following embodiment/feature/aspect, wherein the CD69 antagonist comprises an anti-CD69 antibody and the one or more additional therapy comprises one or more anti-colitis therapy that is at least one anti-diarrheal medication, at least one aminosalicylate, at least one corticosteroid, at least one immunosuppressant, or any combination thereof.

35. The method of any preceding or following embodiment/feature/aspect, wherein the CD69 antagonist comprises an anti-CD69 antibody and the one or more additional therapy comprises one or more anti-hepatitis A therapy that is at least one vaccine, at least one immunoglobulin, or any combination thereof.

36. The method of any preceding or following embodiment/feature/aspect, wherein the CD69 antagonist comprises an anti-CD69 antibody and the one or more additional therapy comprises one or more anti-hepatitis B therapy that is at least one vaccine, at least one interferon, at least one nucleoside reverse transcriptase inhibitor, or any combination thereof.

37. The method of any preceding or following embodiment/feature/aspect, wherein the CD69 antagonist comprises an anti-CD69 antibody and the one or more additional therapy comprises one or more anti-hepatitis C therapy that is at least one vaccine, at least one peginterferon, ribavirin, or any combination thereof.

The present invention can include any combination of these various features or embodiments above and/or below as set forth in sentences and/or paragraphs. Any combination of disclosed features herein is considered part of the present invention and no limitation is intended with respect to combinable features.

The following examples are given to illustrate the nature of the invention. It should be understood, however, that the present invention is not to be limited to the specific conditions or details set forth in these examples. Data can be expressed as mean with SEM. Disease activity index can be statistically analyzed using the Mann-Whitney U test. Differences in parametric data can be evaluated by the Student's t test. Differences of $p<0.05$ are considered statistically significant unless otherwise indicated. The variance of the groups can be tested for equality by F test prior to t test analysis. The role of CD69 is investigated using mouse models of colitis and hepatitis, and it is found that CD69 plays a significant role in the induction of both colitis and hepatitis. Furthermore, administration of anti-CD69 mAb can result in a dramatic reduction in the extent of colitis and hepatitis, establishing that CD69 mAb can be used for the treatment of, or reduction in susceptibility to, colitis and hepatitis, as well as related inflammatory conditions.

EXAMPLES

Example 1

Attenuated DSS-induced colitis in CD69-deficient mice. The aim of this study is to evaluate the role of CD69 in the development of DSS-induced colitis. DSS-induced colitis is achieved by adding 4% DSS to the drinking water to CD69−/−, CD69+/−, and WT mice for 7 days. CD69-deficient (CD69-KO) mice (Murata et al., *Int. Immunol.*, 15:987-992 (2003)) are obtained by backcrossing with BALB/c or C57BL/6 15 times. BALB/c and C57BL/6 mice are purchased from Charles River Laboratories (Tokyo, Japan). All mice are maintained under specific-pathogen-free conditions. All animal care was carried out in accordance with the guidelines of Chiba University and Yamaguchi University.

Colitis was induced in 7 to 8-week-old mice with 4% (w/v) DSS (MW 36,000-50,000; MP Biomedicals, Aurora, Ohio) in the drinking water that was filter-purified (Millipore Corp., Bedford, Mass.) for 7 days. From day 7 onwards, the animals received normal drinking water. DSS consumption, body weight, stool consistency and fecal blood loss were recorded daily. Fecal blood loss was assessed using the Hemocult test (NACALAI TESQUE Inc., Kyoto, Japan). A disease activity index (DAI) (Cooper et al., *Lab. Invest.*, 69:238-249 (1993)) was calculated as described in Table 1. At day 8 or 20, the mice were sacrificed. After measuring colon length, one half of the colon was fixed in 10% (vol./vol.) formalin, paraffin embedded and stained with H&E for histological examination. The other half was frozen in liquid nitrogen and used for cytokine measurements and RNA extraction.

TABLE 1

Scoring of Disease Activity Index

| Score | Weight Loss | Stool consistency[a] | Fecal Blood |
|---|---|---|---|
| 0 | None | Normal | Normal |
| 1 | 1-5% | | |
| 2 | 5-10% | Loose stools | Hemoccult+ |
| 3 | 10-20% | | |
| 4 | >20% | Diarrhea | Gross bleeding |

The disease activity index is the combined scores of weight loss, stool consistency and bleeding divided by three.
[a]Normal stools = well-formed pellets, loose stools = pasty and semi-formed stools which do not stick to the anus, diarrhea = liquid stools that stick to the anus.

Survival rates were significantly increased in CD69−/−, CD69+/− mice compared with those in WT mice after 4% DSS administration (FIG. 1A). Weight, stool consistency and blood loss were scored to calculate the disease activity index (DAI) as described in Table 1. Severity of clinical symptoms was significantly decreased in both CD69−/− and CD69+/− mice compared to WT mice (FIG. 1B). CD69−/− and CD69+/− mice also showed significant protection against DSS-induced colitis as indicated by the weight loss (FIG. 1C).

Figure 2:
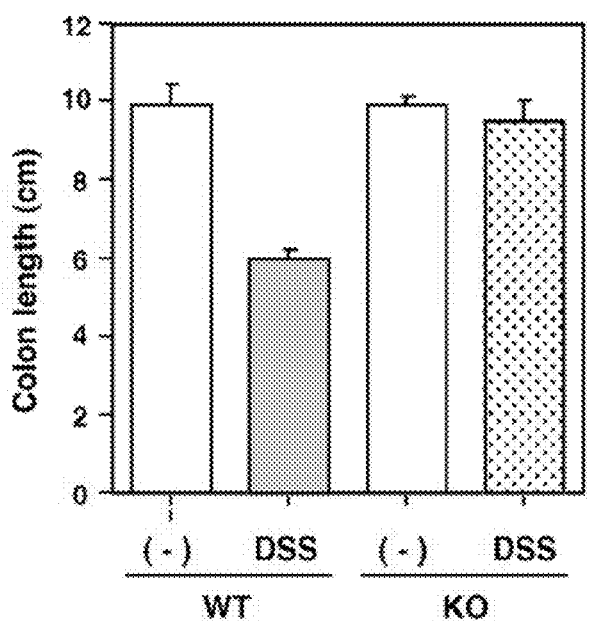
FIG. 2A is a graph that shows data demonstrating that DSS-induced colocaecal damage is reduced in CD69 KO mice. At day 8, colon length of DSS-exposed WT and CD69 KO mice and controls is measured. Data are presented as the mean with SEM (n=12 per group; *p<0.01).
FIG. 2B are photographs of colons and shows further data for the experiment described for FIG. 2A. Representative gross appearance of the colon from each group is shown.
FIG. 2C shows further data for the experiment described for FIG. 2A. Histological sections of inflamed colons are shown. Colons are taken at day 8 from WT and CD69 KO mice receiving DSS in drinking water. Sections are prepared and stained with H&E. Original magnification ×200.
FIG. 2D shows further data for the experiment described for FIG. 2A. Immunohistochemical staining of CD69-positive cells in the colonic tissues of DSS-treated WT mice is shown (original magnification ×400).
Figure 2:
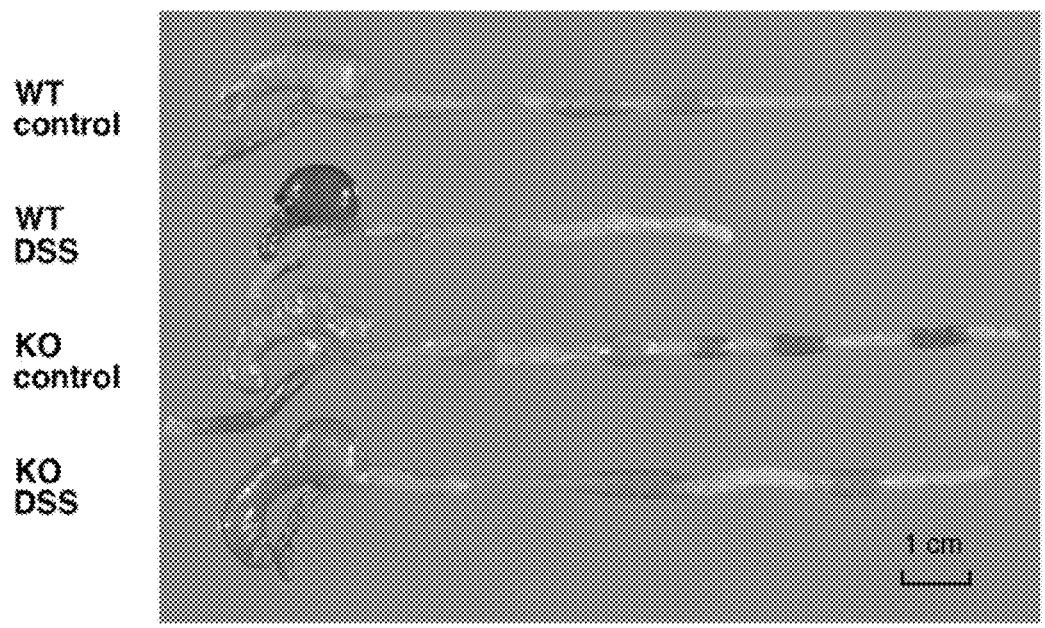

Another sign of disease activity noted in DSS-treated WT mice was colonic shortening (FIGS. 2A, 2B). Macroscopic examinations on day 8 after DSS administration revealed that shortening of colon length of CD69KO mice was significantly inhibited compared with that of WT mice (FIGS. 2A, 2B). On histological examination, crypt damage, ulceration, and infiltration of inflammatory cells were observed in the colons of DSS treated WT mice (FIG. 2C). On the other hand, histological analysis of colons from DSS treated CD69KO mice showed greatly reduced numbers of infiltrating cells and degree of mucosal injury (FIG. 2C). The expression of CD69 in the infiltrating inflammatory cells in the colons of DSS treated WT mice was examined by immunohistochemistry (FIG. 2D). As shown in FIG. 2D, significant expression of CD69 was detected in the infiltrating inflammatory cells in the colons. No significant expression of CD69 was observed in the colons of untreated mice. These results indicate that DSS-induced colitis was attenuated in CD69-deficient mice.

Example 2

DSS-induced colitis was restored partially by cell transfer of wild-type CD4 T cells into CD69-KO mice. To investigate the cellular basis underlying the involvement of CD69 in the pathogenesis of DSS-induced colitis, cell transfer experiments were performed in which whole spleen cells, CD4 T cells, or neutrophils from WT mice were adoptively transferred into CD69KO mice.

Splenic CD4+ T cells from wild-type (WT) BALB/c mice were purified using CD4+ T cell isolation kit (Miltenyi Biotec K.K. of Tokyo) and Auto-MACS sorter (Miltenyi Biotec K.K.), yielding a purity of >98%. Whole spleen cells or CD4+ T cells were administered intravenously through the tail vain to CD69-KO mice ($3 \times 10^7$ cells/mouse) on day −1. For neutrophil preparation, wild-type BALB/c mice were injected intraperitoneally with 2 ml of 4% thioglycolate (Merck, Darmstadt, Germany) and peritoneal neutrophils were recovered 4 h later by collecting peritoneal lavage with 5 ml of saline (Ajuebor et al., J. Immunol., 162:1685-1691 (1999)). Neutrophils in the peritoneal lavage were stained with biotin-conjugated Gr-1 and streptavidin-microbeads, then purified using Auto-MACS sorter, yielding a purity of >90%. Fifteen million neutrophils were injected intravenously into CD69 KO mice on day 0 and 2.

Figure 3:
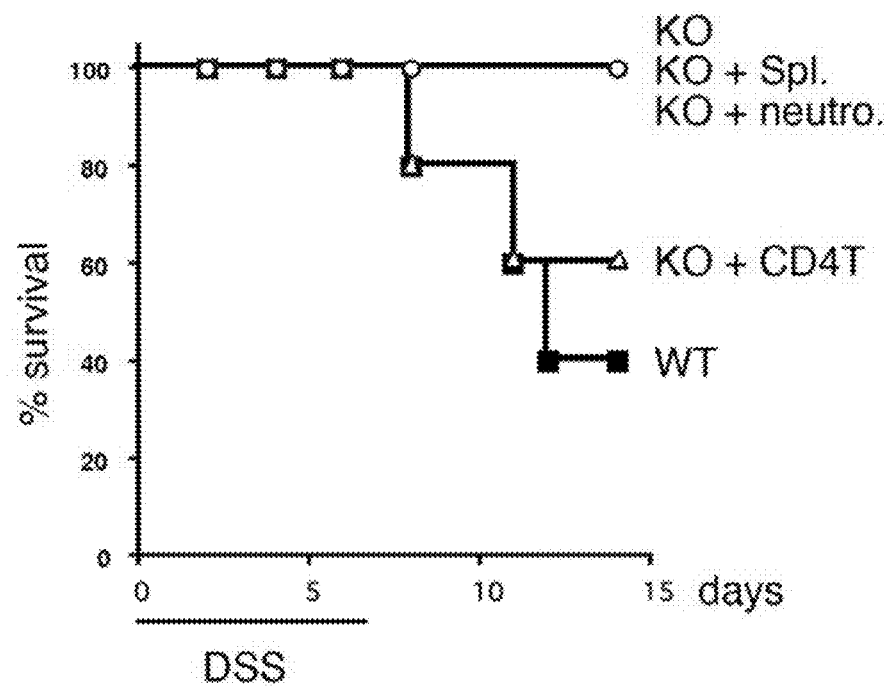
FIG. 3A is a graph that shows data demonstrating that DSS-induced colitis was restored by cell transfer of wild-type CD4 T cells into CD69-KO mice. Survival rates of WT and CD69 KO mice without cell transfer, and CD69-KO mice transferred with whole spleen cells, CD4 T cells or neutrophils during DSS-induced acute colitis are shown. Survival is recorded daily (n=5 per group).
FIG. 3B is a graph that shows further data for the experiment described for FIG. 3A. Changes in the disease activity index over the course of DSS treatment in WT and CD69 KO mice without cell transfer, and CD69-KO mice transferred with whole spleen cells, CD4 T cells or neutrophils are shown. Data are presented as the mean with SD (n=5 per group; *p<0.05).
FIG. 3C is a graph that shows further data for the experiment described for FIG. 3A. Changes in the body weight (%) over the course of DSS treatment in WT and CD69 KO mice without cell transfer, and CD69-KO mice transferred with whole spleen cells, CD4 T cells or neutrophils are shown. Data are presented as the mean with SD (n=5 per group; *p<0.05).
FIG. 3D is a graph that shows further data for the experiment described for FIG. 3A. Colon length of controls and DSS-exposed WT and CD69 KO mice without cell transfer, and CD69-KO mice transferred with whole spleen cells, CD4 T cells or neutrophils at day 8 is measured. Data are presented as the mean with SE (n=5 per group; *p<0.01).
FIG. 3E shows further data for the experiment described for FIG. 3A. Histological sections of inflamed colons are prepared. Colons are taken at day 8 from controls and DSS-exposed CD69 KO mice without cell transfer, and CD69-KO mice transferred with whole spleen cells, CD4 T cells or neutrophils. Sections are fixed and stained with H&E (Original magnification ×200).
Figure 3:
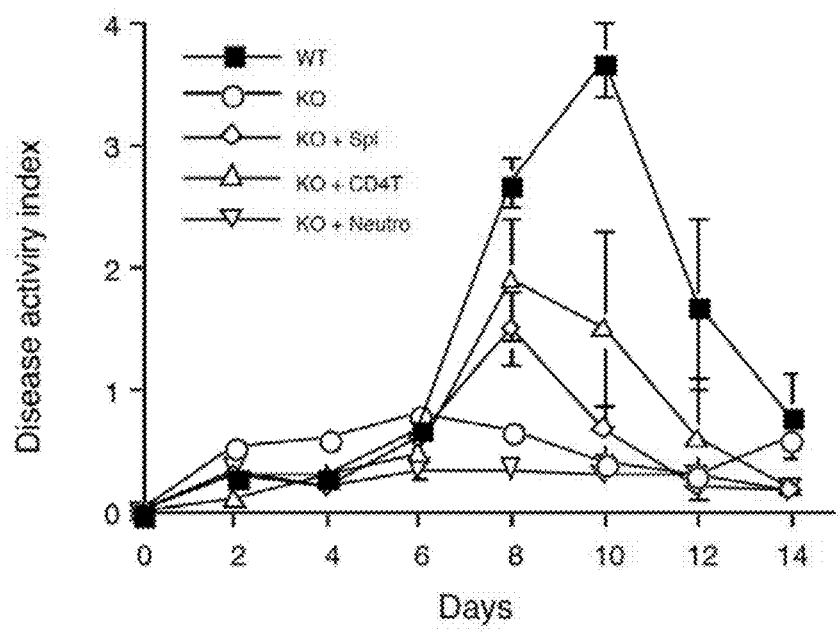

As shown in FIG. 3A, survival rates were significantly decreased by the cell transfer of WT CD4 T cells in CD69KO mice. On the other hand, the decrease of survival rates was not observed by cell transfer of whole spleen cells or neutrophils from WT mice. Severity of clinical symptoms as indicated by the disease activity index (DAI) was substantially restored in CD69KO mice transferred CD4 T cells or whole spleen cells from WT mice (FIG. 3B). No significant changes in the weight loss were observed by cell transfer of whole spleen cells, CD4 T cells or neutrophils from WT mice (FIG. 3C). On the other hand, DSS-induced shortening of colon length was restored in CD69KO mice transferred whole spleen cells, CD4 T cells or neutrophils from WT mice (FIG. 3D). Histological analysis of colons from DSS treated CD69KO mice transferred CD4 T cells or whole spleen cells from WT mice showed substantial restoration of the inflammatory cell infiltration and mucosal injury (FIG. 3E). These results indicated that CD69 expression on CD4 T cells played a role in the induction of the DSS-induced colitis.

Example 3

Attenuation of DSS-induced colitis by anti-CD69 antibody administration. In order to explore the therapeutic effect of the administration of anti-CD69 mAb during DSS-induced colitis, WT BALB/c mice were treated with anti-CD69 mAb or control antibody on day 0, and then survival of each group during DSS-induced colitis was recorded daily. For the anti-CD69 antibody treatment, mice were injected with anti-CD69 mAb (H1.2F3, 500 μg/mouse) intraperitoneally on day 0. The data was presented as representative of at least three individual experiments.

Figure 4:
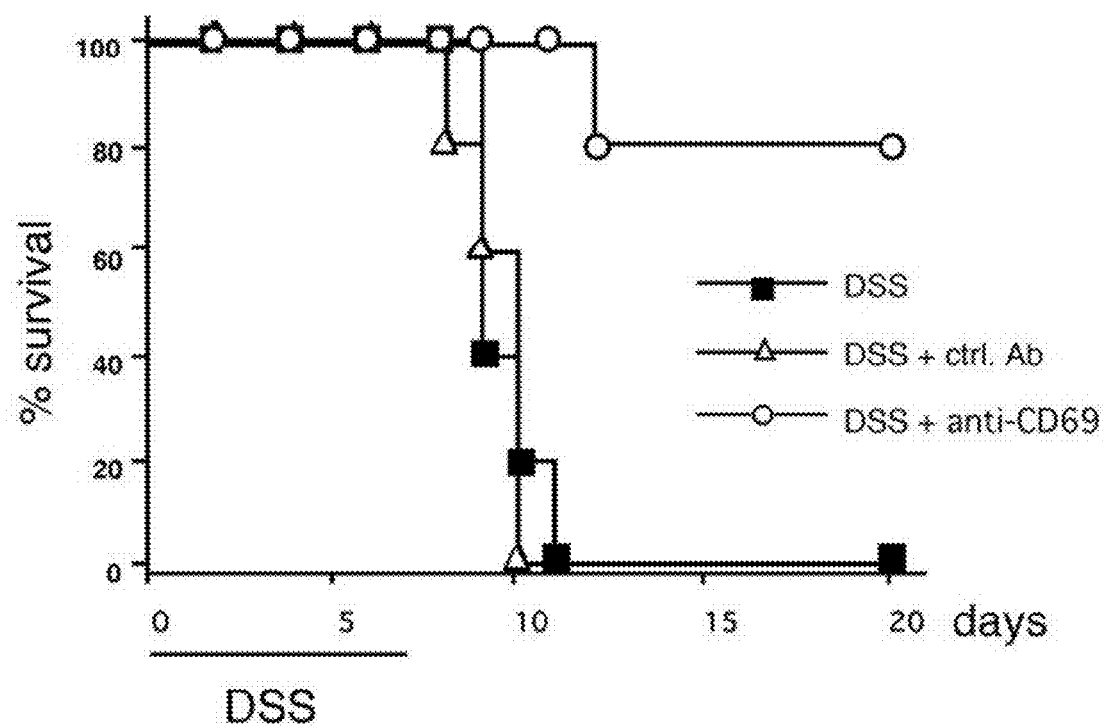
FIG. 4A is a graph that shows data demonstrating the effect of in vivo treatment with anti-CD69 mAb on DSS-induced colitis. WT BALB/c mice are treated with anti-CD69 mAb or control hamster IgG on day 0, Survival of each group during DSS-induced colitis is recorded daily (n=5 per group).
FIG. 4B is a graph that shows further data for the experiment described for FIG. 4A. Changes in the disease activity index over the course of DSS treatment in WT mice treated with anti-CD69 mAb or control hamster IgG are shown. Data are presented as the mean with SD (n=5 per group; *p<0.05).
FIG. 4C is a graph that shows further data for the experiment described for FIG. 4A. Changes in the body weight (%) (over the course of DSS treatment in WT mice treated with anti-CD69 mAb or control hamster IgG are shown. Data are presented as the mean with SD (n=5 per group; *p<0.05).
FIG. 4D is a bar graph that shows further data for the experiment described for FIG. 4A. Colon length of controls and DSS-exposed WT mice treated with anti-CD69 mAb or control hamster IgG are shown. Data are presented as the mean with SE (n=5 per group; *p<0.01).
FIG. 4E shows further data for the experiment described for FIG. 4A. Histological sections are prepared. Colons are taken at day 8 from controls and DSS-exposed WT mice treated with anti-CD69 mAb or control hamster IgG. Sections are fixed and stained with H&E (original magnification ×200).
Figure 4:
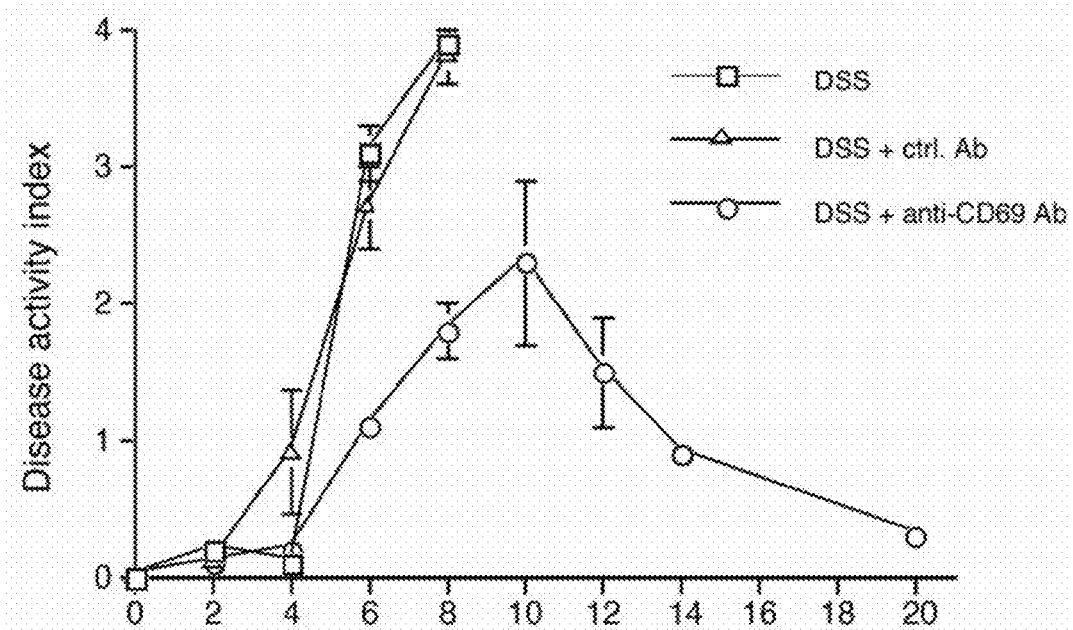

Survival rates were significantly increased by in vivo anti-CD69 treatment compared with those in control antibody-treated WT mice after DSS administration (FIG. 4A). Severity of clinical symptoms indicated by the disease activity index (DAI) was substantially protected by anti-CD69 mAb treatment (FIG. 4B). The weight loss was slightly protected by anti-CD69 mAb treatment and recovered in survived mice at day 20 (FIG. 4C). On the other hand, DSS-induced shortening of colon length was not protected by anti-CD69 mAb treatment (FIG. 4D). On histological examination, crypt damage, ulceration, and infiltration of inflammatory cells were greatly reduced by anti-CD69 mAb treatment (FIG. 4E). Thus, a therapeutic effect of anti-CD69 antibody was indicated in the DSS-induced colitis model.

Example 4

Cytokine, chemokine and chemokine receptor expression. This example demonstrates that the CD69-mediated protection observed in murine DSS colitis is reflected by changes in mRNA expression of cytokines and chemokines related to ulcerative colitis. Mice were sacrificed at day 8 and the colon tissues were harvested. Whole colonic RNA was isolated, reverse transcribed into cDNA and the expressions of IL-1β, IL-6, IL-10, CCR2, CCR3, CCL2, CCL4 and CCL5 are determined by real-time quantitative PCR. The amounts of mRNAs are normalized by the HPRT signal in the respective samples. Whole colonic RNA was extracted using Trizol (Invitrogen). RNA concentration was determined spectrophotometrically and quality was assessed after agarose electrophoresis. cDNA synthesis and Quantitative RT-PCR is performed (Nigo et al., Proc. Natl. Acad. Sci. U.S.A., 103:2286-2291 (2006)). The primers for Taq Man probes for the detection of IL-1β, IL-6, IL-10, CCR2, CCR3, CCL2, CCL4, CCL5 and HPRT were purchased from Applied Biosystems. The expression was normalized by the HPRT signal.

Figure 5:
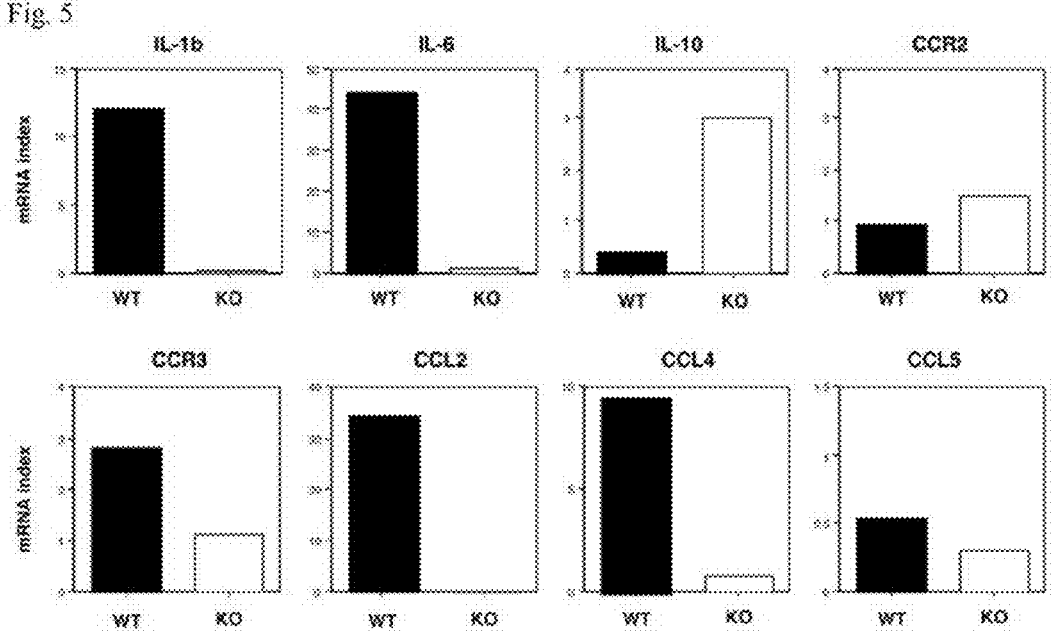
FIG. 5 is a series of bar graphs that show data demonstrating the expression of cytokines, chemokines and their receptor mRNA in the colons of DSS-treated mice. Five mice per group are treated as described in experiment described for FIG. 1A. Mice are sacrificed at day 8 and the colon tissues are harvested. Whole colonic RNA is isolated, reverse transcribed into cDNA and the expressions of IL-1β, IL-6, IL-10, CCR2, CCR3, CCL2, CCL4 and CCL5 are determined by real-time quantitative PCR. The amounts of mRNAs are normalized by the HPRT signal in the respective sample. PCR is performed in triplicate for each sample. There are no significant increases in mRNA expression in either the untreated WT or CD69 KO mice. The data presented are representative of three individual experiments.

After 8 days of DSS exposure, a significant increase in the expression levels of IL-1β, IL-6, CCR2, CCR3, CCL2, CCL4 and CCL5 mRNA was seen in the WT mice (FIG. 5). However, mRNA expression levels of IL-1β, IL-6, CCR3, CCL2 and CCL4 were not increased in DSS treated CD69KO mice (FIG. 5). Interestingly, mRNA expression level of IL-10 was significantly increased in DSS treated CD69KO mice compared with that in DSS treated WT mice.

Example 5

Attenuated ConA-induced hepatitis in CD69-deficient mice. The physiological roles of CD69 in ConA-induced hepatitis using CD69-deficient mice was examined. Con A (Sigma) was dissolved in pyrogen-free PBS and intravenously injected into C57BL/6 mice through the tail vein at a dose of 10 mg/kg. Sera from individual mice were obtained 12 h after ConA injection. Serum aminotransferase [alanine aminotransferase (ALT) and aspartate aminotransferase (AST)] activities was measured by the standard photometric method using an automatic analyzer (Fuji Film Medical, Tokyo, Japan).

The hepatitis was evaluated by measuring the levels of aspartate aminotransferase (AST) and alanine aminotransferase (ALT) in plasma 12 h after ConA injection (10 mg/ml). In the ConA-induced hepatitis model, the levels of AST and ALT increased 4 h after ConA injection, and thereafter increased rapidly reaching the peak values at 12 h time point.

Figure 6:
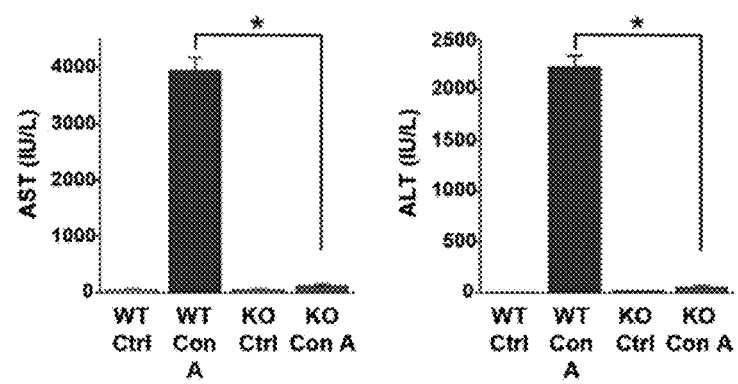
FIG. 6A is a set of bar graphs that show data demonstrating the attenuation of ConA-induced hepatitis in CD69-deficient mice. Plasma AST and ALT levels in CD69KO and WT mice 12 h after ConA (10 mg/kg, i.v.) injection are shown. The results are expressed as mean±SD (n=5; *p<0.05), compared with WT mice.
FIG. 6B shows further data for the experiment described for FIG. 6A. The livers are collected 12 hours after ConA injection, and the liver damage is evaluated by H&E staining.
Figure 6:
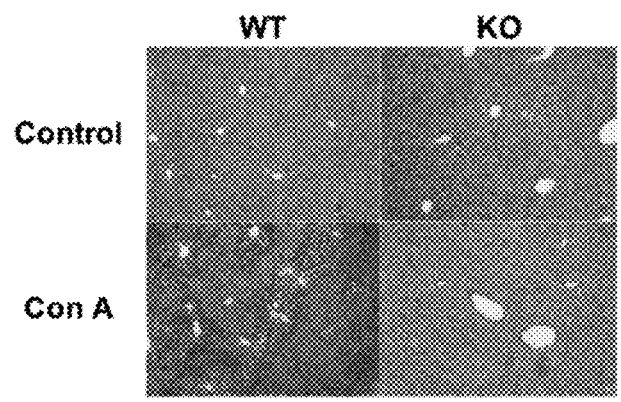

The levels of AST and ALT were decreased in CD69-deficient mice in comparison to WT mice (FIG. 6A). A histological analysis of the liver was also performed. After ConA-injection, liver damage accompanied with increased apoptotic hepatocytes was apparently attenuated in CD69-deficient mice as compared to that observed in WT mice (FIG. 6B).

Example 6

Attenuation of ConA-induced hepatitis by anti-CD69 antibody administration. The administration of anti-CD69 mAb was examined to determine whether such administration inhibits liver injury induced by intravenous injection of ConA. For the anti-CD69 antibody treatment, mice were injected with anti-CD69 mAb (H1.2F3, 400 µg/mouse) intraperitoneally 30 minutes before the injection of ConA. For histological analysis, the livers from individual mice were fixed in 10% formalin, embedded in paraffin, sectioned, and stained with H&E for histological examination. Specimens are examined under a light microscope.

Figure 7:
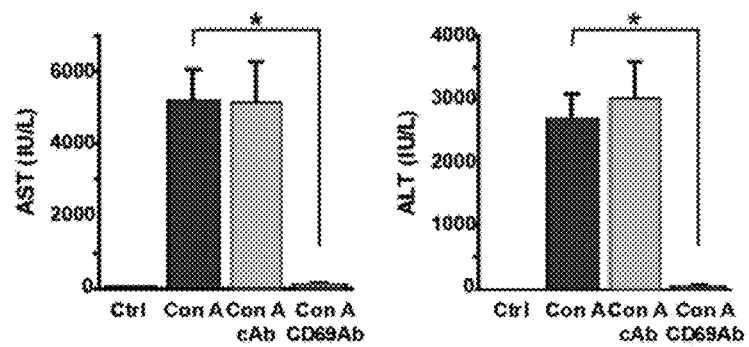
FIG. 7A is a set of bar graphs that show data demonstrating the attenuation of ConA-induced hepatitis by anti-CD69 antibody administration. Plasma AST and ALT levels in ConA-induced hepatitis in mice are shown. WT C57BL/6 mice are treated with anti-CD69 mAb (400 μg/mouse) or control hamster IgG intraperitoneally 30 min before the injection of ConA. The plasma is collected 12 h after ConA injection. The results are expressed as mean±SD (n=5; *p<0.05).
FIG. 7B shows further data for the experiment described for FIG. 7A. The livers are collected 12 h after ConA injection and the liver damage is evaluated by H&E staining.
Figure 7:
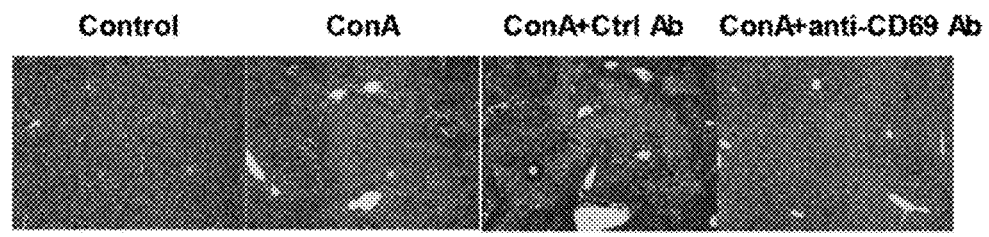

The administration of anti-CD69 mAb (400 µg/mouse) before the injection of ConA significantly suppressed the increased levels of AST and ALT. The histological changes in the liver 12 h after ConA injection were also evaluated. Histological examination of the liver by H&E staining revealed focal or massive severe necrosis in the area between the central veins and the portal tracts of ConA-injected mice (FIG. 7B). Pre-administration of anti-CD69 mAb clearly suppressed the severe necrosis and apoptosis in the liver (FIG. 7B). The treatment of normal mice with anti-CD69 mAb alone had no effects on the levels of AST and ALT. Thus, a therapeutic effect of anti-CD69 antibody was indicated in the ConA-induced hepatitis model. IFN-gamma producing CD4 T cells and NKT cells also appeared to be good therapeutic target cells in ConA-induced hepatitis.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of treating or reducing colitis comprising: administering one or more antagonistic anti-CD69 antibodies or polypeptides comprising an antigen-binding fragment of the antagonistic anti-CD69 antibodies to a subject, wherein the subject has been diagnosed with colitis, in an amount effective to treat or reduce colitis.

2. The method of claim 1, wherein the amount effective to treat or reduce colitis is measured by monitoring at least one symptom of colitis.

3. The method of claim 2, wherein the at least one symptom comprises epithelial cell lesions, acute inflammation, diarrhea, rectal bleeding, weight loss, or any combinations thereof.

4. The method of claim 2, further comprising:
continuing administration if the at least one symptom persists, falls within a given range, or remains above or below a threshold value; or
discontinuing administration if the at least one symptom fails to persist, fails to fall within a given range, or no longer remains above or below a threshold value.

5. The method of claim 1, wherein the one or more antagonistic anti-CD69 antibodies comprise a chimeric antibody.

6. The method of claim 1, wherein the one or more antagonistic anti-CD69 antibodies comprise a humanized antibody.

7. The method of claim 1 wherein the one or more antagonistic anti-CD69 antibodies comprise a completely humanized antibody.

8. The method of claim 1 wherein the one or more antagonistic anti-CD69 antibodies comprise a monoclonal antibody.

9. The method of claim 1 wherein the one or more antagonistic anti-CD69 antibodies comprise a polyclonal antibody.

10. The method of claim 1 wherein the one or more antagonistic anti-CD69 antibodies comprise a single-chain antibody.

11. The method of claim 1 wherein the one or more antagonistic anti-CD69 antibodies or polypeptides are conjugated to a functional agent to form an immunoconguate.

12. The method of claim 11, wherein the functional agent is a cytotoxic agent that is an antibiotic, a radioactive isotope, a nucleolytic enzyme, a toxin, or any combination thereof.

13. The method of claim 1, wherein the one or more antagonistic anti-CD69 antibodies or polypeptides bind to an extracellular domain of CD69.

14. The method of claim 1, wherein two or more antagonistic anti-CD69 antibodies or polypeptides comprising an antigen-binding fragment of the antagonistic anti-CD69 antibodies are administered.

15. The method of claim 1, wherein at least one antagonistic anti-CD69 antibody or polypeptide comprising an antigen-binding fragment of the antagonistic anti-CD69 antibody is administered in combination with one or more additional therapies directed to colitis.

16. The method of claim 15, wherein the combination of the at least one antagonistic anti-CD69 antibody or polypeptide comprising an antigen-binding fragment of the antagonistic anti-CD69 antibody and the one or more additional therapies act synergistically to treat or reduce colitis.

17. The method of claim 15, wherein the one or more additional therapies comprise one or more anti-colitis therapies that is at least one anti-diarrheal medication, at least one aminosalicylate, at least one corticosteroid, at least one immunosuppressant, or any combination thereof.

* * * * *